(12) United States Patent
Majeti et al.

(10) Patent No.: US 11,344,575 B2
(45) Date of Patent: *May 31, 2022

(54) VASCULAR CALCIFICATION PREVENTION AND TREATMENT

(71) Applicant: Summit Innovation Labs, LLC, Norwood, OH (US)

(72) Inventors: Satyanarayana Majeti, Liberty Township, OH (US); Haile Mehansho, Hamilton, OH (US); Ghebre Egziabher Tzeghai, Wyoming, OH (US)

(73) Assignee: Summit Innovation Labs, LLC, Norwood, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/649,084

(22) Filed: Jul. 13, 2017

(65) Prior Publication Data

US 2018/0042962 A1 Feb. 15, 2018

Related U.S. Application Data

(60) Provisional application No. 62/374,983, filed on Aug. 15, 2016.

(51) Int. Cl.
*A61K 33/42* (2006.01)
*A61K 31/355* (2006.01)
(Continued)

(52) U.S. Cl.
CPC ............... *A61K 33/42* (2013.01); *A61K 9/08* (2013.01); *A61K 31/07* (2013.01); *A61K 31/12* (2013.01);
(Continued)

(58) Field of Classification Search
CPC .......... A61K 33/42; A61K 9/08; A61K 31/07; A61K 31/12; A61K 31/122; A61K 31/355; A61K 31/593; A61K 31/353; A61K 33/06; A61K 45/06; A61K 9/0053; A61K 9/0095; A61K 33/14
See application file for complete search history.

(56) References Cited

U.S. PATENT DOCUMENTS 4,217,342 A * 8/1980 Gaffar ...................... A61K 8/19
424/48
5,849,337 A 12/1998 Dixon
(Continued)

FOREIGN PATENT DOCUMENTS

CN 1477959 A 2/2004
CN 1956734 A 5/2007
(Continued)

OTHER PUBLICATIONS

Ganio (Year: 2010).*
Vormann (Year: 2003).*
Khurana S, et al. (2013) Polyphenols: Benefits to the Cardiovascular System in Health and in Aging, Nutrients. 5 (10): 3779-3827.
Movahed, Ali, et al. (2013) Antihyperglycemic Effects of Short Term Resveratrol Supplementation in Type 2 Diabetic Patients, Hindawi Publishing Corporation Evidence-Based Complementary and Alternative Medicine, vol. 2013, Article ID 851267, 11pages.
Schurgers LJ, et al. (2007) Regression of Warfarin-Induced medical elastocalcinosis by high intake of Vitamin K in rats. Blood, 109: 2823-2831.
Chinese Office Aciton dated Jun. 16, 2021 in reference to Application No. 201780050345.X filed Jul. 24, 2017.
"How to make a pregnant woman happy" p. 189, released Feb. 28, 2006.

(Continued)

*Primary Examiner* — Jeffrey S Lundgren
*Assistant Examiner* — Ibrahim D Bori
(74) *Attorney, Agent, or Firm* — Dinsmore & Shohl LLP

(57) ABSTRACT

The invention encompasses compositions and methods for effectively interfering, reducing and preventing conversion of vascular smooth muscle cells (VSMCs) and circulating stem cells to osteoblastic bone-like cells, thereby reducing and/or preventing vascular calcification (VC) or calcium mineral (hydroxyapatite) deposition in the vasculature. The severity and extent of calcification in the major arteries reflect atherosclerotic plaque burden and strongly predict cardiovascular morbidity and mortality. The present inventive compositions used for administration to human and other mammalian subjects comprise select actives that inhibit, interfere or regulate the biochemical processes leading to such calcification and include (1) at least one agent that modulates expression and/or activity of peroxisome activated protein receptor gamma (PPAR-$\gamma$); (2) at least one agent that inhibits expression and/or suppresses activity of one or more of the osteogenic transcription factors (Cbf$\alpha$1/Runx2, Osterix, Msx2) and $\beta$-catenin signaling; (3) at least one agent that inhibits expression and/or suppresses activity of one or more of bone morphogenetic proteins (BMPs: BMP 2 and 4), alkaline phosphatase (ALP), and osteocalcin; (4) at least one agent that inhibits the activity of Reactive Oxygen Species (ROS); and (5) at least one agent that suppresses one or more of inflammatory mediators including interleukins IL-1$\alpha$, IL-1$\beta$, IL-6, NF-$\kappa$B, TNF-$\alpha$, matrix metalloproteinases (MMPs) and prostaglandin E2 (PGE2). The compositions may further comprise at least one agent that promotes expression and/or carboxylation of matrix Gla protein (MGP). Advantageously, these select actives include materials such as phytonutrients, vitamins and minerals that have been broadly used in food and drink products and are safe for human and pet/animal consumption. Compositions with such combinations have the ability to prevent, treat and reverse VC not only in coronary arteries but also in other tissues capable of undergoing undesirable calcification. In addition the present compositions are effective against associated conditions or contributory factors/inducers to VC, including diabetes, obesity, hypertension, inflammation, oxidative stress, osteoporosis and arthritis.

4 Claims, No Drawings

(51) Int. Cl.
*A61K 31/12* (2006.01)
*A61K 31/07* (2006.01)
*A61K 31/122* (2006.01)
*A61K 31/353* (2006.01)
*A61K 9/08* (2006.01)
*A61K 31/593* (2006.01)
*A61K 33/06* (2006.01)
*A61K 45/06* (2006.01)
*A61K 9/00* (2006.01)
*A61K 33/14* (2006.01)

(52) U.S. Cl.
CPC .......... *A61K 31/122* (2013.01); *A61K 31/353* (2013.01); *A61K 31/355* (2013.01); *A61K 31/593* (2013.01); *A61K 33/06* (2013.01); *A61K 45/06* (2013.01); *A61K 9/0053* (2013.01); *A61K 9/0095* (2013.01); *A61K 33/14* (2013.01)

(56) References Cited

U.S. PATENT DOCUMENTS

| | | | |
|---|---|---|---|
| 6,210,701 B1* | 4/2001 | Darland | A61K 36/53 424/439 |
| 9,138,453 B2 | 9/2015 | Zhao-Wilson | |
| 9,364,447 B2 | 6/2016 | Vermeer | |
| 2006/0166948 A1 | 7/2006 | Vermeer | |
| 2007/0048296 A1 | 3/2007 | Kajander et al. | |
| 2008/0242690 A1* | 10/2008 | Tripp | A61K 36/82 514/280 |
| 2009/0087501 A1* | 4/2009 | Cummins | A61K 36/15 424/729 |
| 2010/0021533 A1* | 1/2010 | Mazed | A61K 36/54 424/450 |
| 2012/0121730 A1* | 5/2012 | Singh | A61P 11/02 424/682 |
| 2013/0017182 A1 | 1/2013 | Lukina | |
| 2015/0056176 A1 | 2/2015 | Jankowitz et al. | |
| 2015/0118304 A1 | 4/2015 | Cornblatt et al. | |
| 2016/0193306 A1 | 7/2016 | Rabovsky et al. | |
| 2017/0000856 A1 | 1/2017 | Holstein et al. | |

FOREIGN PATENT DOCUMENTS

| | | | |
|---|---|---|---|
| CN | 101239168 A | 8/2008 | |
| EP | 2626077 A2 | 8/2013 | |
| WO | 2004019923 A1 | 3/2004 | |
| WO | WO-2004019923 A1 * | 3/2004 | ................ A61P 9/14 |
| WO | 2008006582 A1 | 1/2008 | |
| WO | WO-2008006582 A1 * | 1/2008 | ........... A61K 36/575 |
| WO | WO-2014019923 A1 * | 2/2014 | ............. F03D 80/82 |
| WO | 2015176153 | 11/2015 | |

OTHER PUBLICATIONS

P. Roman-Garcia, S. Barrio-Vazquez, J. L. Fernandez-Martin et al., "Natural antioxidants and vascular calcification: a possible benefit," Journal of Nephrology, vol. 24, No. 6, pp. 669-672, 2011.

K. E. Beazley, S. Eghtesad, and M. V. Nurminskaya, "Quercetin attenuates warfarin-induced vascular calcification in vitro independently from matrix GLA protein," Journal of Biological Chemistry, vol. 288, No. 4, pp. 2632-2640, 2013.

A. M. De Oca, F. Guerrero, J. M. Martinez-Moreno et al., "Magnesium inhibits Wnt/β-catenin activity and reverses the osteogenic transformation of vascular smooth muscle cells," PLoS One, vol. 9, No. 2, p. e89525, 2014.

P. Zhang, Y. Li, Y. Du, G. Li L. Wang, and F. Zhou, "Resveratrol ameliorated vascular calcification by regulating Sirt-1 and Nrf2," Transplantation Proceedings, vol. 48, No. 10, pp. 3378-3386, 2016.

Mexican Office Action dated Sep. 15, 2021 in reference to Application No. MX/a/2019/001811 filed on Jul. 24, 2017.

* cited by examiner

VASCULAR CALCIFICATION PREVENTION AND TREATMENT

CROSS REFERENCE TO RELATED APPLICATIONS

This application claims the benefit of U.S. Provisional Application No. 62/374,983 filed on Aug. 15, 2016.

FIELD OF THE INVENTION

The present invention relates to compositions and methods for the treatment and prevention of calcification and/or plaque-based conditions and diseases associated with accumulation of calcium phosphate or crystalline hydroxyapatite deposits on tissues. The present compositions comprise combinations of select actives that provide additive or synergistic benefits for these diseases and conditions, in particular cardiovascular diseases and associated conditions or contributory factors/inducers including diabetes, obesity, hypertension, inflammation, oxidative stress, osteoporosis and arthritis. Advantageously, these select actives include materials such as phytonutrients, vitamins and minerals that have been broadly used in food and drink products and are safe for human and pet/animal consumption.

BACKGROUND OF THE INVENTION

Biomineralization refers, generally to the formation of discrete and organized inorganic crystalline structures within macromolecular extracellular matrices, including for example, the formation of calcium phosphate or crystalline hydroxyapatite. Such biomineralization process in which calcium phosphate is deposited in tissue is referred to as calcification. Normal deposition of calcium occurs in only two places: bone and teeth, which are living tissues that are in a constant state of renewal. The process of bone formation involves osteoblast cells which are specialized, terminally differentiated products of mesenchymal stem cells. Osteoblasts synthesize very dense, crosslinked collagen, and several additional specialized proteins in much smaller quantities, including osteocalcin and osteopontin, which compose the organic matrix of bone. In organized groups of connected cells, osteoblasts produce a calcium and phosphate-based mineral, hydroxyapatite, which is deposited in a highly regulated manner into the organic matrix forming a very strong and dense mineralized tissue, i.e., bone/skeleton. This mineralized skeleton is the main support for the bodies of air breathing vertebrates. It also is an important store of minerals for physiological homeostasis including both acid-base balance and calcium/phosphate maintenance.

Bone is a dynamic tissue that is constantly being reshaped by osteoblasts, which produce and secrete matrix proteins and transport mineral into the matrix. The maintenance of bone first requires old bone to be dissolved by cells called "osteoclasts." The activity of osteoclasts should not be too high as large holes may develop that would weaken the bone and lead to bone degradation and osteoporosis. The holes left by osteoclastic activity are prepared for remodeling by osteoblast cells. The osteoblasts secrete a protein called osteocalcin, which when activated (through carboxylation) enables new calcium to be laid down into the bone for structural density and integrity.

Calcification other than in bone and teeth is termed systemic calcification and is undesirable in that it is a serious health risk. A characteristic of normal aging involves systemic calcification meaning that calcium that is supposed to be deposited in the bones is instead being lodged in soft tissues throughout the body such as heart valves, glands, and blood vessels where calcium deposits do not belong. Thus, many age-related diseases can be linked to calcification including kidney and bladder stones, pancreatic duct stones, arthritis, cataracts, bone fractures, bone spurs, wrinkled skin, senility and importantly, heart valve insufficiency and other heart or circulatory diseases. Heart disease is associated with abnormal (pathological) deposition of calcium in the form of hydroxyapatite crystals in multiple coronary tissues including: (1) the inner lining of the arteries (the intima) where atherosclerotic plaque accrues; (2) the middle muscle layer of arteries (smooth muscle calcification); and (3) the heart valves, especially the aortic valve causing aortic stenosis. Calcium accumulation in the arteries and other coronary tissues is generally referred to as vascular calcification (VC).

Heart disease, specifically atherosclerosis, is the leading cause of disability and death in the United States and globally. Many factors are involved in the initiation and progression of atherosclerosis. Homocysteine or oxidized low-density lipoprotein (LDL) can cause inflammation of the inner arterial lining (the endothelium). In response, the endothelium produces collagen that forms a cap over the inflamed site. These endothelial collagen caps attract calcium that accumulates, i.e., calcifies, forming a hard material called plaque, which resembles bone. This is why atherosclerosis is sometimes referred to as "hardening of the arteries." The resulting calcified plaque causes the arteries to become narrower and stiff and reduces and/or blocks blood flow to the various organs, which can subsequently lead to heart attack and stroke. This condition is particularly prevalent as people get older. However, even though the prevalence of heart disease increases with age, it is in fact a disease of all ages (3). For instance, the prevalence of mortality due to heart disease among men 1-24 years, 25-64 years, and older than 65 years, is 4.6%, 32.7% and 55.8%, respectively. [Piko B. "Epidemiology of Cardiovascular Disease (CVD)". University of Pittsburgh, Slides 1-33 ppt].

Therefore, there is a critical need for therapeutic and preventive compositions and methods against unwanted calcification in the body, importantly against vascular calcification. However, since systemic calcification is associated with many other diseases and is prevalent among all ages, its control, prevention and reversal are urgent and key clinical needs in overall human health and healthcare, and importantly to address the enormous cost associated with such healthcare. It is estimated that in the US alone, the direct costs plus time lost associated with cardiovascular healthcare amounted to a staggering $320.1 billion in 2011. [Mozaffaranian D, et. al. (2015) "Heart Disease and Stroke Statistics", *Circulation*, vol 131, e29-e322.]

SUMMARY OF THE INVENTION

The invention encompasses compositions and methods for effectively reducing and preventing unwanted systemic calcification, i.e., deposition of calcium as hydroxyapatite in soft tissues rather than just in bones and teeth. In particular, the invention focuses on reducing and/or preventing vascular calcification (VC), i.e., calcium mineral (hydroxyapatite) deposition in the vasculature or arteries. This is accomplished by totally addressing the multiple mechanisms that lead to such systemic calcification. The invention includes compositions that effectively suppress, regulate or interfere with the differentiation of vascular smooth muscle cells (VSMCs) and circulating stem cells to osteoblast-like cells, thereby reducing or preventing vascular calcification. The severity and extent of calcification in the major arteries reflect atherosclerotic plaque burden and strongly predict cardiovascular morbidity and mortality. The inventive compositions used for administration to human and other mammalian subjects comprise actives that inhibit, interfere or regulate the biochemical processes leading to such calcification and include (1) at least one agent that modulates expression and/or activity of peroxisome activated protein receptor gamma (PPAR-$\gamma$); (2) at least one agent that inhibits expression and/or suppresses activity of one or more of the osteogenic transcription factors (Cbf$\alpha$1/Runx2, Osterix, Msx2) and $\beta$-catenin signaling; (3) at least one agent that inhibits expression and/or suppresses activity of one or more of bone morphogenetic proteins (BMPs: BMP 2 and 4), alkaline phosphatase (ALP), and osteocalcin; (4) at least one agent that inhibits the activity of Reactive Oxygen Species (ROS); and (5) at least one agent that suppresses one or more of inflammatory mediators including interleukins IL-1$\alpha$, IL-1$\beta$, IL-6, NF-$\kappa$B, TNF-$\alpha$, matrix metalloproteinases (MMPs) and prostaglandin E2 (PGE2). The compositions further comprise at least one agent that promotes expression and/or carboxylation of matrix Gla protein (MGP). It is to be understood that any one of the agents used herein may provide multiple activities or functions; thus in some embodiments the present combinations may comprise less than five or six different agents. Compositions with such combinations have the ability to prevent, treat and even reverse calcification not only in coronary arteries but also in other tissues capable of undergoing or susceptible to undesirable calcification.

DETAILED DESCRIPTION OF THE INVENTION

All percentages used herein are by weight of the composition, unless otherwise specified. The ratios used herein are molar ratios of the overall composition, unless otherwise specified. All measurements of e.g., weights, pH values, etc. are made at 25° C. with standard equipment, unless otherwise specified.

As used in this disclosure and the appended claims, the singular forms "a," "an" and "the" include plural referents unless the context clearly dictates otherwise. As used herein, "about" is understood to refer to numbers in a range of numerals. Moreover, all numerical ranges herein should be understood to include all integers, whole or fractions, within the range. The compositions disclosed herein may lack any element that is not specifically disclosed herein. Herein, "comprising" and its variants mean that other steps and other ingredients which do not affect the end result can be added. The terms encompass the terms "consisting of" and "consisting essentially of". Thus, the disclosure of an embodiment using the term "comprising" includes a disclosure of an embodiment "consisting essentially" of and an embodiment "consisting" of the referenced components. Any embodiment disclosed herein can be combined with any other embodiment disclosed herein.

As used herein, the word "include," and variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the terms "prevent", "prevention" and variants includes reduction of risk and/or severity of vascular calcification and/or any other referenced condition. The terms "treatment", "treat", "ameliorate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measures. The terms "treatment," "treat" and "alleviate" are further intended to include the dietary management of a disease or condition or the dietary management for prophylaxis or prevention a disease or condition. A treatment can be patient- or doctor-related.

As used herein, a "therapeutically effective amount" is an amount that prevents a deficiency, treats a disease or medical condition in an individual or, more generally, reduces symptoms, manages progression of the diseases or provides a nutritional, physiological, or medical benefit to the individual. The therapeutically effective amount that is required to achieve a therapeutic effect will, of course, vary with the particular composition, the route of administration, the age and the condition of the recipient, and the particular disorder or disease being treated.

By "safe and effective amount" as used herein means a sufficient amount of an active agent to provide the desired benefit while being safe and will vary with the particular condition being treated, the age and physical condition of the patient being treated, the severity of the condition, the duration of treatment, the nature of concurrent therapy, the specific form of the agent(s) employed, and the particular vehicle from which the agent(s) are applied.

As used herein, "animal" includes, but is not limited to, mammals, which includes but is not limited to, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human, having or at risk for a medical condition that can benefit from the treatment.

The term "phytonutrients" or "phytochemicals" are used herein to denote natural chemical compounds that are found in many plant foods and refers to any compound produced by a plant that imparts one or more health benefits to the user. "Phyto" refers to the Greek word for plant. These chemicals help protect plants from germs, fungi, bugs, and other threats.

The terms, "food product", "food composition", "nutritional composition", "dietary supplement" and variants as used herein, are understood to include any number of optional additional ingredients, including conventional additives, for example, one or more proteins, carbohydrates, fats, vitamins, minerals, acidulants, thickeners, buffers or agents for pH adjustment, chelating agents, colorants, emulsifiers, excipients, flavoring and sweetening agents, osmotic agents, preservatives, stabilizers, sugars, sweeteners, and/or texturizers, acceptable excipients and/or carriers for oral consumption. The optional ingredients can be added in any suitable amount.

The term "carriers" refer to one or more compatible solid or liquid excipients or diluents which are suitable for oral administration and consumption. By "compatible," as used herein, is meant that the components of the composition are capable of being commingled without interaction in a manner which would substantially reduce the composition's stability and/or efficacy. Suitable excipient and/or carriers for ingestible products include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, vegetable gums, lactose, methyl cellulose, povidone, carboxymethyl cellulose, corn starch, and the like (including mixtures thereof). Preferred carriers include calcium carbonate, magnesium stearate, maltodextrin, and mixtures thereof.

Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof.

The compositions of the present invention may be in various forms including ingestible solid forms such as capsules, tablets, pills, gummies, gelcaps, or granules and powder such as teas and drink mixes. The compositions may also be prepared as a liquid solution, emulsion, concentrate, gel, and the like for beverage and like products.

The present compositions may also be prepared for use in topical applications such as for the oral cavity, skin, hair, scalp and nails. By "topical composition", "oral, hair, skin, scalp or nail care composition" as used herein means products which in the ordinary course of usage are not intentionally swallowed for purposes of systemic administration of particular therapeutic agents, but are rather retained in the oral cavity or other body surfaces/tissues for a time sufficient to contact substantially all such dental, mouth, skin, scalp, hair or nail surfaces and/or tissues to deliver the intended benefits.

The topical oral care composition of the present invention may be in various forms including toothpaste, dentifrice, tooth powder, topical oral gel, mouthrinse, denture product, mouthspray, mousse, foam, lozenge, oral tablet, and chewing gum. Examples of composition forms for the care of the skin, scalp, hair or nail include lotions, creams, gels, cleansers, scrubs, shampoos, rinses, rinse-off or leave-in conditioners, mousses, hairsprays, ointments, tinctures and salves. Carriers and excipients for these topical products are well known in the art. For example, conventional additives in oral care compositions include but are not limited to fluoride ion sources; anti-calculus or anti-tartar agents; antimicrobial agents such as stannous salts, cetyl pyridinium chloride (CPC), flavor oils and others; buffers; abrasives such as silica; bleaching agents such as peroxide sources; alkali metal bicarbonate salts; thickening materials; humectants; water; surfactants; titanium dioxide; flavor system; sweetening agents; xylitol; coloring agents, and mixtures thereof.

For pet and animal care, the present compositions may be formulated for example as tablets, foods, chews and toys. The active agent(s) may be incorporated for example, into a relatively supple but strong and durable material such as rawhide, ropes made from natural or synthetic fibers, and polymeric articles made from nylon, polyester or thermoplastic polyurethane. As the animal chews, licks or gnaws the product, incorporated active agents are released into the animal's oral cavity and ingested. In pet food embodiments, the active agent(s) may be incorporated as an ingredient or admixed into a pet food such as for example, a kibbled, semi-moist, or canned food. The present compositions may also be incorporated into other pet care products including nutritional supplements and drinking water additives.

The various ingredients and the excipient and/or carrier are mixed and formed into the desired form using conventional techniques. For example, the tablet or capsule of the present invention may be coated with an enteric coating that dissolves at a pH of about 5.0 to 9.0. Suitable enteric coatings that dissolve at a higher pH in intestine but not in the stomach include cellulose acetate phthalate, phospholipid bilayers and others. Further materials are well known in the art and are readily chosen by one skilled in the art based on the physical, aesthetic and performance properties desired for the compositions being prepared. Details on techniques for formulation and administration may be found in *Remingtons' Pharmaceutical Sciences* (18th Edition, 1990); *Cosmetic and Toiletry Formulations* ($2^{nd}$ Edition, 1989); *The International Cosmetic Ingredient Directory and Handbook* ($8^{th}$ Edition, 2000).

Active and other ingredients useful herein may be categorized or described herein by their therapeutic and/or nutritional benefit or their postulated mode of action or function. However, it is to be understood that the active and other ingredients useful herein can, in some instances, provide more than one therapeutic benefit or function or operate via more than one mode of action. Therefore, classifications herein are made for the sake of convenience and are not intended to limit an ingredient to the particularly stated application or applications listed.

In one embodiment, the present compositions comprise combinations of select actives that provide additive or synergistic benefits for cardiovascular health. Advantageously, these actives are naturally occurring chemicals extracted from plants and are safe for consumption. The benefit to cardiovascular health from these combinations of actives results from holistically addressing the multiple mechanisms that lead to vascular calcification.

Vascular calcification (VC) or arterial calcium accumulation is characterized by deposition of calcium phosphate in the form of hydroxyapatite crystals and other calcium phosphate salts. VC is a complex and tightly regulated metabolic process sharing many features with the mineralization process in skeletal or bone tissue. Both bone and VC development and metabolism are related to an imbalance of local and systemic inhibitors and inducers of calcification. The major and critical steps involved in the development of VC include:
(1) transformation of normal/healthy vascular smooth muscle cells (VSMCs) and/or circulating stem cells to osteoblast/bone forming-like cells and
(2) calcium deposition in the form of hydroxyapatite crystals.

The first committed and prerequisite step in the process of vascular calcification is the transformation of the VSMCs and other cell types such as circulating stem cells, to osteoblast-like cells. These are cells that can form bone-like structures. The ability to undergo reversible differentiation is characteristic of the VSMC phenotype; these cells are in their differentiated, contractile form at baseline but respond to the above pathological stimuli by entering a proliferative, synthetic state to produce extracellular matrix (ECM) and to undergo osteogenic differentiation. This transformation is triggered for example, by repeated exposure to multiple chronic diseases, including hypertension, kidney disease, diabetes, inflammation, hyperphosphatemia/hypercalcemia and oxidative stress. In a normal or healthy state, VSMCs are in their differentiated, contractile form; however, when repeatedly exposed to the above pathological inducers, they express proteins including bone morphogenic proteins (BMPs: BMP2 and BMP4), osteogenic transcription factors [Runt-related transcription factor 2 (Runx2) also known as core-binding factor subunit alpha-1 (Cbfα-1), Osterix and), and signaling pathways (Wnt/β-catenin), which all promote the differentiation of the VSMCs to osteoblastic-like cells. These osteoblast-like cells share many properties with bone-forming cells, including increased alkaline phosphatase (ALP) activity and expression of osteocalcin, osteonectin, and osteopontin (OPN). Increased expression of ALP has been shown to promote the differentiation of VSMCs by increasing cellular phosphate concentration [Giachelli C M (2009), "The Emerging Role of Phosphate in Vascular Calcification". *Kidney Int.* 75(9): 890-897].

Because of the complexity of the overall process by which VC develops involving multiple stimuli or triggers and multiple mechanisms by which these triggers cause transformation, preventing and/or treating VC and consequently, coronary heart disease has remained a serious and inadequately addressed global public health problem. The following are reasons for the current lack and/or limited success in the fight against these conditions.

Current approaches to VC prevention/treatment are focused on treating individual stimuli with specific drug(s) (e.g., thiazide diuretics and beta-blockers for hypertension; metformin for diabetes; nonsteroidal and steroidal anti-inflammatory drugs for inflammation, and statins for high cholesterol). In other words previous approaches are not holistic.

Furthermore, the treatment drugs currently used to treat these chronic diseases do have side effects that could be detrimental to the overall health of the patient using them.

The current single disease treatments are not designed to treat/prevent VC by inhibiting the important and critical step, i.e., the differentiation of normal/healthy VSMCs and other stem cells to osteoblast-like cells.

Thus, there is unmet need for developing products/drugs that prevent/treat VC by inhibiting the transformation of VSMCs to osteoblast-like cells. The invention described herein encompasses safe and effective products that block the transformation of VSMCs to osteoblast-like cells by suppressing the expression of the multiple inducer and inhibitor proteins involved in such undesired transformation.

Vascular calcification is primarily the result of a process which starts from the differentiation of smooth muscle cells and other circulating cells to osteoblast-like cells. These osteoblast-like cells are able to secrete various components of the extracellular matrix (ECM) and deposit calcium salts, primarily hydroxyapatite, very similar to what is observed in bone under the action of osteoblasts Like the osteoblasts of bone tissue, these differentiated cells are able to achieve an extracellular calcium phosphate deposit, leading schematically to ossification of the arterial wall. The risk of acute vascular accident mortality is largely correlated with the calcification of the walls of large arteries, particularly at the valves.

Extensive research reported in the literature provides evidence that VC is a tightly regulated process, with competition between factors that trigger or promote calcification and those that inhibit mineralization. [See e.g., Zhu D, et al. (2012), "Mechanisms and Clinical Consequences of Vascular Calcification". *Frontiers in Endocrinology*, 3:1-12; Johnson R C et al. (2006), "Vascular Calcification Pathological Mechanisms and Clinical Implications". *Circ. Research:* 1044-1059]. Positive regulators (i.e., triggers or inducers) of VC are those that induce the formation of "osteoblast-like" cells in the vasculature and the upregulation of transcription factors that are crucial in the programming of osteogenesis. Among the inducers that have been reported are high calcium/phosphate/glucose, uremia, osteoporosis, pro-inflammatory cytokines, lipids, macrophages, apoptosis, transglutaminase-2, high Vitamin D, transforming growth factor beta (TGF-β), vascular endothelial growth factor (VEGF), parathyroid hormone (PTH), glucocorticoids and warfarin. Negative regulators (i.e., inhibitors or suppressors) are molecules that blood vessels normally express to inhibit mineralization, such as pyrophosphate and matrix Gla protein (MGP). Lack of these molecules means "loss of inhibition", which then leads to spontaneous vascular calcification. Other negative regulators include fetuin-A, osteopontin, osteoprotegerin, statins, Vitamin K, bisphosphonates, fibroblast growth factor 23 (FGF23)/Klotho protein and insulin-like growth factor 1 (IGF-1).

Based on available evidence from the literature, it is believed that the following are key VC triggers in that they contribute to the critical step of transforming normal VSMCs and other cells to osteoblast-like cells that can form bone-like or hard deposits in soft tissues.

Hyperphosphatemia and Hypercalcemia

High phosphate level promotes VC by up-regulating the expression of a signaling pathway (β-catenin), BMPs and transcription factors, Runt-related transcription factor 2 (Runx2) also known as core-binding factor subunit alpha-1 (CBFα-1), and Osterix, which are mediators of the differentiation of VSMCs and other cells to osteoblast-like cells. (See e.g., Johnson R C et al. Ibid., Jimi, E, et al. (2010), "Molecular mechanisms of BMP-induced bone formation: Cross-talk between BMP and NF-κB signaling pathways in osteoblastogenesis", *Japanese Dental Science Review*, 46(1): 33-42.]

In vitro studies reported in the literature demonstrated that high phosphate levels comparable to those seen in hyperphosphatemic individuals directly promoted osteogenic differentiation of VSMC, as indicated by increased expression of bone-related marker proteins and loss of SMC marker genes. Likewise, elevating Ca levels in the culture media to levels considered hypercalcemic (>2.6 mM) with or without addition of high phosphate leads to enhanced mineralization and phenotypic transition of vascular smooth muscle cells. Hyperphosphatemia and hypercalcemia increased the secretion of matrix vesicles in human VSMC and generation of a mineralization-competent extracellular matrix such as seen in bone formation. [See e.g., Giachelli C M, (2004), "Vascular Calcification Mechanisms". *JASN.* 15(12): 2959-2964; Jono S, et al. (2000), "Phosphate regulation of vascular smooth muscle cell calcification". *Circ. Res.,* 87: E10-E17; Yang H, et al (December 2004), "Elevated extracellular calcium levels induce smooth muscle cell matrix mineralization in vitro". *Kidney Int.* 66(6): 2293-98].

Anti-Coagulant Therapy with e.g., Warfarin (Coumadin):

Warfarin has been demonstrated to trigger VC by inhibiting the activation of matrix Gla protein (MGP) via γ-carboxylation and by inducing the expression of signaling pathways (β-catenin), osteogenic transcription factors (Runx2/Cbfα-1, Osterix), and BMPs, known mediators of the transformation of VSMCs to osteoblast-like cells even in normal calcium and clinically acceptable phosphate levels. In addition, it has been shown that warfarin treatment of VSMCs resulted in uncarboxylated (Gla-deficient) MGP, which does not have the important functionality of suppressing osteochondrogenic transdifferentiation of vascular smooth muscle cells (by inhibiting the expression of bone morphogenetic proteins 2 and 4) and directly inhibiting calcium-crystal growth. [See e.g., Zhu D, et al. (2012); Schurgers L J, et al. (2007), "Post-translational modifications regulate matrix Gla protein function: importance for inhibition of vascular smooth muscle cell calcification". *J. Thromb. Haemost.* 5: 2503-2511].

Inflammation:

Repeated inflammation triggers VC by (a) up-regulating the expression of differentiation promoters of VSMCs, BMPs and osteogenic transcription factors (Runx2 and Osterix), and (b) suppressing the expression of vascular differentiation inhibitor proteins such as osteoprotegerin [See e.g., Shao J S, et al. (2006), "Inflammation and the Osteogenic Regulation of Vascular Calcification: A Review & Perspective". *Hypertension* 55: 579-592].

Oxidative Stress:

Oxidative stress is the net balance between oxidant production and anti-oxidative activity. Pro-oxidants include reactive nitrogen species and reactive oxygen species (ROS) such as superoxide anions and hydrogen peroxide. Increased oxidative burden results in the formation of oxidized LDLs, which have been shown to stimulate differentiation of VSMCs into a bone phenotype including upregulation and activation of BMP2 and Runx2/Cbfα1 in concert with matrix mineral deposition. [See e.g., Byon C H, et al. (2008), "Oxidative Stress Induces Vascular Calcification through Modulation of the Osteogenic Transcription Factor Runx2 by AKT Signaling". *J. Biol. Chem.* 283: 15319-15327; Mody N, et al. (2001), "Oxidative stress modulates osteoblastic differentiation of vascular and bone cells". *Free Radic. Biol. Med.* 31: 509-519]. Additionally, reactive oxygen species (ROS) signaling can induce other markers of osteoblastic differentiation such as an increase in alkaline phosphatase (ALP) activity. ALP is a functional phenotypic marker of osteoblasts, and ALP activity is often used as a molecular marker for vascular calcification, as it is an early indicator of extracellular matrix (ECM) deposition. ALP activity is crucial to hydroxyapatite formation during endochondral ossification as well as in vascular calcification. The mechanism by which ALP modulates vascular calcification is by decreasing levels of inorganic pyrophosphate; pyrophosphate is a substrate for ALP and a recognized potent inhibitor of vascular calcification.

Because the oxidative stress that induces osteoblastic differentiation of VSMCs is often the result of the inflammatory process, inflammatory cytokines themselves have been implicated in vascular calcification. It has also been suggested that TNF-α has a crucial role in vascular calcification. The osteoblastic differentiation of VSMCs, as assayed by ALP activity and mineral deposition, is induced by TNF-α in a dosage-dependent manner. This induction by TNF-α is mediated through the cAMP (cyclic Adenosine monophosphate) pathway, and cAMP stimulates the osteoblastic differentiation of VSMCs. Furthermore, TNF-α enhances the DNA binding of Cbfα1/Runx2, activated protein 1, and cAMP responsive element binding protein, which are important transcription factors in osteoblastic differentiation. [See e.g., Shioi A, et al. (2002), "Induction of bone-type alkaline phosphatase in human vascular smooth muscle cells: Roles of tumor necrosis factor-alpha and oncostatin M derived from macrophages". *Circ. Res.* 91: 9-16; Tintut Y, et al. (2000), "Tumor necrosis factor-alpha promotes in vitro calcification of vascular cells via the cAMP pathway". *Circulation* 102: 2636-2642; Tintut Y, et al. (1998), "cAMP stimulates osteoblast-like differentiation of calcifying vascular cells: Potential signaling pathway for vascular calcification". *J. Biol. Chem.* 273: 7547-7553.]

Hypertension:

Hypertension is associated with vascular changes characterized by remodeling, endothelial dysfunction and hyperreactivity. Cellular processes underlying these perturbations include altered vascular smooth muscle cell growth and apoptosis, fibrosis, hypercontractility and calcification. Vascular calcification is accelerated by hypertension and also contributes to hypertension. Among the many factors involved in the hypertensive vascular phenotype, angiotensin II (ANG II) has been demonstrated to be important. ANG II is a peptide hormone that causes vasoconstriction and a subsequent increase in blood pressure. In an in vitro study of calcification of human aortic and mouse VSMCs, ANG II was demonstrated to induce the differentiation of VSMCs into osteoblastic phenotype via a receptor activator of nuclear factor-κB ligand (RANKL) pathway and reactive oxygen species (ROS) production. In the presence of osteogenic-inducible medium, ANG II increased Cbfα1 protein level in VSMCs along with increase in RANKL levels, calcium deposition, calcified nodule formation and ROS production. Additionally the RANKL system was shown to decrease the calcification inhibitor, matrix Gla protein (MGP), in VSMC, and to elevate BMP-2 expression, thus further contributing to vascular calcification. RANKL also potentiated the VSMC differentiation into osteoblast-like cells by inducing the expression of the master transcription factors: Cbfα1 and Msx2. Furthermore, the role of ANG II in vascular calcification was confirmed since treatment with an ANG II receptor blocker (ARB)), significantly decreased the calcification and the mRNA levels of RANK and RANKL, associated with the inhibition of BMP-2 and cbfα1 [See e.g., Jia G, et al. (2012) "Role of Matrix Gla Protein in Angiotensin II-Induced Exacerbation of Vascular Calcification". *Am J Phys. Heart Circ. Physiol.*, H523-H532; Osako M K, et al (2013), "Cross-Talk of Receptor Activator of Nuclear Factor-κB Ligand Signaling With Renin-Angiotensin System in Vascular Calcification". *Arteriosclerosis, Thrombosis, and Vascular Biology,* 33: 1287-1296.]

In addition to angiotensin, another factor that has been implicated in the pathogenesis of hypertension is the Endothelin family of peptides, specifically endothelin-1 (ET-1), which is an even more potent vasoconstrictor than ANG II. ET-1 is released from endothelial as well as other cell types. When over-expressed, ET-1 contributes to high blood pressure (hypertension) and other cardiovascular disorders including vascular calcification. An in vitro study of β-glycerophosphate-induced calcification found an upregulated endothelin gene expression as well as an increased production of endothelin in calcified arteries. The results of this study showed that calcium content, $Ca^{+2}$ uptake and alkaline phosphatase (ALP) activity were increased in calcified VSMCs, compared with controls. Further, when a specific ET-1 receptor antagonist was used to incubate with calcifying VSMCs, calcification of VSMCs was reduced, thus strongly suggesting the involvement of ET-1 in the pathogenesis of vascular calcification. [See e.g., Wu S Y, et al. (2003), "Endothelin-1 is a potent regulator in vivo in vascular calcification and in vitro in calcification of vascular smooth muscle cells". *Peptides* 24: 1149-1156; Essalihi R, et al. (2004), "Phenotypic modulation of vascular smooth muscle cells during medial arterial calcification: a role for endothelin?" *J. Cardiovasc. Pharmacol.* 44 Suppl 1: S147-150.]

Diabetes:

Hyperglycemia promotes VC in one aspect through its ability to cause chronic inflammation. In addition, reactive oxygen species (ROS) and advanced glycation end products (AGEs), which are induced by diabetes, have been shown to increase the expression of cytokine (NF-κB) and transcription factor (Runx2/Cbfα1). Both NF-κB and Runx2 are known to promote differentiation of VSMCs to osteoblast-like cells. In addition, diabetes also down regulates the expression of MGP, which is an inhibitor of the BMP-mediated differentiation of VSMCs to osteoblast-like cells. Studies in humans have demonstrated that vascular calcification in diabetes is associated with increased expression of bone matrix proteins and alkaline phosphatase (ALP). In vitro studies using bovine VMSCs have demonstrated that high glucose increased the expression of the osteoblast transcription factor Runx2/Cbfα-1, its downstream protein osteocalcin, BMP-2 and ALP activity. These results suggest that the increased vascular calcification in diabetes is at least partially due to the direct effects of hyperglycemia on VSMC via multiple mechanisms. [See e.g., Di Marco, et al. (2013). "Diabetes Alters Activation and Repression of Pro- and Anti-inflammatory Signaling Pathways in the Vasculature". *Frontiers in Endocrinology/Diabetes*, 4: 1-6; Paneni F, et al. (2014). "Molecular Mechanism of Vascular Dysfunction and Cardiovascular Biomarkers in Type 2 Diabetes". *Cardiovasc. Diagn. Ther.* 4: 324-332; Chen N X, et al. (2006) "High glucose increases the expression of Cbfα1 and BMP-2 and enhances the calcification of vascular smooth muscle cells". *Nephrol. Dial. Transplant.* (21(12): 3435-3442.]

Chronic Kidney Disease (CKD):

Patients with CKD have an altered calcium and phosphate and metabolism, i.e., hyperphosphatemia and/or hypercalcemia, which as discussed above are important contributors to the progression of vascular calcification. Extracellular phosphate promotes the mineralization of VSMCs in both dosage- and time-dependent manners by increasing the influx of phosphate into VSMCs, which leads to the induction of osteoblastic differentiation factors such as Cbfα1/Runx2, BMP-2, osteocalcin (OC) and β-catenin signaling, which are involved in mediating the transformation of VSMCs to osteoblast-like cells. Elevated extracellular phosphate levels have also been shown increase alkaline phosphatase (ALP) and accelerate mineralization of VSMCs. Furthermore, the uremic state in CKD is characterized by increased oxidative stress, which produces reactive oxygen species (ROS) such as superoxide anions and hydrogen peroxide. The ROS hydrogen peroxide was recently shown to promote osteogenic transdifferentiation of VSMCs, including upregulation and activation of Runx2/Cbfα1 in concert with matrix mineral deposition. [See e.g., Massy Z A and Drueke T B (2012), "Magnesium and outcomes in patients with chronic disease: focus on vascular calcification, atherosclerosis and survival". *Clin Kidney*, 5 (suppl 1): i52-i61; Rong S, et al. (2014), "Vascular Calcification in Chronic Kidney Disease is induced by Morphogenetic Protein-2 via a Mechanism Involving the Wnt/B-catenin Pathway". *Cell Physiol. Biochem.*, 34: 2049-2060; Jono S, et al. (2000), "Phosphate regulation of vascular smooth muscle cell calcification". *Circ. Res.* 87: E10-E17; Mizobuchi M. et al. (July 2009), "Vascular Calcification: The Killer of Patients with Chronic Kidney Disease". *J. Amer. Soc. Nephrology.* 20:7, 1453-1464.]

Osteoporosis:

The association of osteoporosis with vascular calcification has been widely reported. In human patients with osteoporosis, loss of bone tissue from the skeleton has been observed to occur at the same time as formation of bone-like structures in the artery wall. In studies with rodents, vascular calcification and osteoporosis have been shown to co-exist under at least three conditions: deficiency of osteoprotegerin, an osteoclast inhibitory factor, deficiency of dietary essential fatty acids and hyperlipidaemia. In vitro and in vivo studies have shown that oxidized lipids not only promote mineralization of vascular cells but they also inhibit mineralization of bone cells. Low density lipoprotein (LDL) levels correlate with both coronary and aortic valve calcification progression, and LDL proteins accumulate in calcified aortic valves. Hyperlipidemia is associated with rapid progression of coronary calcification, and lipid-lowering therapy reduces progression of both coronary and valvular calcification. Studies have further shown that oxidized lipids induce osteoblastic differentiation in vascular cells and hyperlipidemia reduces bone mineral density in mice. From these studies, it appears that lipid accumulation and oxidation lead to a reversal of the normal regional control of biomineralization, promoting calcification of soft tissue and osteolysis of bone, accounting for the paradox of bone-like formation in the arteries of patients who are losing bone from their skeletons. [See e.g., Demer L L (2002) "Vascular calcification and osteoporosis: inflammatory responses to oxidized lipids". *Int. J. Epidemiol.* 31:737-741; Parhami F, et al. (1997) "Lipid oxidation products have opposite effects on calcifying vascular cell and bone cell differentiation. A possible explanation for the paradox of arterial calcification in osteoporotic patients". *Arterioscler. Thromb. Vasc. Biol.* 17:680-87; Bucay N, et al. (1998), "Osteoprotegerin-deficient mice develop early onset osteoporosis and arterial calcification". *Genes Dev.* 12:1260-68; Farhat G N and Cauley J A (2008), "The Link Between Osteoporosis and Cardiovascular Disease". Clinical *Cases in Mineral and Bone Metabolism*, 5:19-34; Cannata-Andia J B, et al. (2011), "The connections between vascular calcification and bone health". *Nephrology Dialysis Transplantation*, 26(11): 3429-3436.]

Recent data suggest that the co-incidence of vascular calcification and osteoporosis, i.e., bone loss and increased fracture risk is not simply age-associated, rather that these disorders are biologically linked. During the development of vascular calcification, the transition of vascular smooth muscle cells towards an osteoblast-like phenotype promotes the release of the vesicular structures and mineralization within these structures is promoted by several players, including those related to mineral metabolism, like phosphorus and calcium, which influence either the supersaturation within the structure or the expression of osteogenic factors. Calcium and phosphorus levels are increased as bone is lost from the skeleton in osteoporosis. As discussed above, both high phosphate and high calcium levels individuals directly promote osteogenic differentiation of VSMCs and enhanced mineralization. Hyperphosphatemia and hypercalcemia increase the secretion of matrix vesicles in human VSMC and generation of a mineralization-competent extracellular matrix such as seen in bone formation. The mineral observed in calcium deposits of atherosclerotic plaques has a very similar chemical composition to hydroxyapatite crystals which form the inorganic bone matrix. Calcifiable vesicles have been isolated from human atherosclerotic aortas, suggesting that these may be involved in mineral deposition, similar to "extracellular matrix vesicles" that are secreted from chondrocytes and osteoblasts and are involved in initial bone mineralization. Calcified plaques have also been shown to express several bone matrix proteins such as type I collagen, gla (gamma carboxyglutamate)-containing proteins such as osteocalcin (bone-gla protein) and matrix-gla protein, bone morphogenetic proteins, (BMP-2 and -4), osteopontin, osteonectin, and bone sialoprotein. Osteogenic cells, called calcifying vascular cells (CVCs), have been identified in atherosclerotic plaques. These are a subpopulation of vascular smooth muscle cells (VSMC) that are capable of osteoblastic differentiation. When stimulated by BMP-2 and BMP-4, these cells begin expressing osteoblast genes including alkaline phosphatase, collagen I, and osteocalcin which are needed for bone formation. Other cells involved in bone metabolism including osteoclast-like cells, chondrocyte-like cells, and hematopoietic bone marrow cells also seen in plaques.

Calcification Inhibitors:

Soft tissues contain the following key biological calcium deposition inhibitors to protect from calcification. In addition to formation of osteoblast-like cells in the vessel wall and osteogenesis induced by the metabolic insults described above by which vascular calcification progresses, a lack of inhibitors of calcification is another important mechanism behind vascular calcification. Lack of these molecules results in "loss of inhibition of mineralization" thus leading to spontaneous vascular calcification. [See e.g., Zhu D, et al. (2012) Ibid.]; Johnson R C et al. (2006) Ibid.]; Beazley K E, et al. (2013). "Quercetin Attenuates Warfarin-induced Vascular Calcification in Vitro Independently from Matrix Gla Protein". *J. Biol. Chem.* 288: 2632-2640; Montes de Oca A, et al. (2014). "Magnesium Inhibits Wnt/β-catenin Activity and Reverses the Osteogenic Transformation of Vascular Smooth Muscle Cells". *PLOS ONE* 9 (2): e89525; Mizobuchi M. et al. (July 2009) Ibid.]

Matrix γ-Carboxyglutamic Acid (Gla) Protein (MGP):

Matrix-Gla-protein (MGP) is mainly secreted by chondrocytes and vascular smooth muscle cells (VSMCs). This potent inhibitor of vascular calcification need to undergo 2 post-transcriptional steps to be fully active: one phosphorylation of 3 serine residues (on 5) and a carboxylation of 5 glutamate residues (on 9). Like other "Gla" proteins, this carboxylation is vitamin K dependent. Several forms of MGP thus circulate in the plasma, some of them being totally inactive (the unphosphorylated and uncarboxylated MGP), some others being partially or fully active, according to the number of phosphorylated or carboxylated sites. Non- or under-carboxylated MGP due mainly to vitamin-K insufficiency and/or long-term warfarin treatment accelerates the development of vascular calcification. Carboxylated MGP can prevent calcification by inhibition of the pro-osteogenic activity of bone morphogenetic proteins (BMPs 2 and 4) through their sequestration and by direct inhibition of hydroxyapatite formation in the extracellular matrix.

Osteoprotegerin (OPG):

Osteoprotegerin (OPG) is a protein identified as a member of the tumor necrosis factor receptor gene superfamily and is a secreted factor that has been shown to inhibit osteoclast differentiation and activation. OPG is a physiological regulator of normal bone mass. This has been by demonstrated in experiments wherein targeted deletion of OPG in mice results in severe, early-onset osteoporosis. The early-onset osteoporosis observed in these mice is a result of increased bone resorption associated with increased numbers and activity of osteoclasts. Loss of OPG also resulted in calcification of the aorta and renal arteries, which are sites of endogenous OPG expression in normal animals, thus indicating an additional role for OPG to regulate pathological calcification of arteries. [See e.g., Bucay N, et al. (1998), "Osteoprotegerin-deficient mice develop early onset osteoporosis and arterial calcification". *Genes Dev.* 12:1260-68; Price P A, et al. (2001), "Osteoprotegerin Inhibits Artery Calcification Induced by Warfarin and by Vitamin D". *Arteriosclerosis, Thrombosis, and Vascular Biology* 21: 1610-1616.]

Another finding is that OPG is down-regulated in calcified VSMC. OPG protects the cells against calcification by reducing alkaline phosphatase (ALP) activity as well as by exerting an inhibitory effect on apoptosis. This is important as apoptotic bodies may act as nucleation sites for the crystallization of apatite. Importantly, OPG inhibits the transformation of VSMCs to osteoblastic-like cells by suppressing (a) inflammation-mediated osteogenic differentiation of vascular cells, (b) vascular calcium accumulation and (c) alkaline phosphatase activity, which would promote an increase of phosphate concentration, which together with increased calcium would trigger VC.

Osteopontin (OPN):

OPN is an acidic phosphoprotein that is expressed in mineralized tissues and inhibits the mineralization of tissues by blocking hydroxyapatite formation and by activating osteoclast function. Although OPN is not expressed in normal vessels, abundant OPN is found in calcified arteries, indicating that OPN is a regulator of vascular calcification. OPN inhibits the mineralization of VSMCs by binding to the mineralized crystal surface. Phosphorylation of OPN is necessary for its inhibitory effect on the mineralization of VSMCs. The function of OPN is believed to represent an adaptive response to counteract the progression of vascular calcification.

Pyrophosphates (PPi):

Pyrophosphate is a major inhibitor of vascular calcification and acts by inhibiting hydroxyapatite crystal formation. PPi is generated from the hydrolysis of nucleotide triphosphates by the nucleotide pyrophosphatase phosphodiesterase family (NPP). The lack of PPi generation has been shown to cause extended medial layer calcification and to induce aortic ring calcification. Moreover, the mechanisms of PPi-dependent control of vascular calcium accrual encompass the inhibition of VSMC osteochondrogenic transdifferentiation.

Fetuin:

Fetuin-A is a $Ca^{2+}$-binding glycoprotein found in serum and produced predominantly by the liver. Whereas MGP, OPN, and OPG are local factors involved in vascular calcification and function at the site of calcification, fetuin-A is a circulating inhibitor of vascular calcification. VSMCs can take up serum fetuin-A and pool it in intracellular membrane-bound matrix vesicles, which are released from VSMCs and become the central point for mineral nucleation. These released vesicles have abundant fetuin-A and prevent the ability of membrane-bound matrix vesicles to form hydroxyapatite crystal.

In addition to the inhibitors above, the peroxisome proliferator-activated receptor-γ (PPAR-γ) is of significance. PPAR-γ is a ligand-activated transcriptional factor belonging to the nuclear receptors superfamily and known to play important roles in glucose, lipid and bone metabolism as well as in the vascular system. PPAR-γ in the vascular wall have been reported to protect against development of atherosclerosis and several experimental findings suggest that PPAR-γ may protect against cardiovascular calcification. As discussed, the critical step in vascular calcification is the differentiation of normal VSMCs and other vascular cell types to an osteoblast-like or bone-forming phenotype that go through pro-osteogenic pathways. PPAR-γ appears to be highly expressed during atherosclerotic lesion formation, suggesting that increased PPAR-γ expression may be a vascular compensatory response. Additionally, PPAR-γ impairs differentiation of progenitor cells into osteoblasts, and inhibition of PPAR-γ increases differentiation of embryonic stem cells to osteoblasts. Thus PPAR-γ activity inhibits osteogenesis and vascular calcification by controlling cell differentiation and the pro-osteogenic signaling pathway. Also, oxidative stress and inflammation appear to play an important role in vascular calcification and PPAR-γ has anti-inflammatory activity in addition to its antioxidant effects. [See e.g., Wang N, et al. (2011). "Role of peroxisome proliferator-activated receptor-γ in atherosclerosis: an update". *Circ J.* 75:528-535; Qu A, et al. (2012), "Disruption of endothelial peroxisome proliferator-activated receptor γ accelerates diet-induced atherogenesis in LDL receptor-null mice". *Arterioscler. Thromb. Vasc. Biol.* 32:65-73; Yamashita A, et al. (2006) "Transient suppression of PPAR-gamma directed ES cells into an osteoblastic lineage". *FEBS Lett.* 580:4121-4125; Woldt, E et al. (2012), "PPARγ counteracts LRP1-induced vascular calcification by Inhibiting a Wnt5a Signaling pathway". *Nat. Commun.* 3:1077.]

The molecular mechanisms by which the above VC inducers cause differentiation of VSMCs to osteoblast-like are highly regulated. As discussed in the literature, VC occurs via very distinctive but overlapping mechanisms. The process involves production of proteins that either promote bone formation or suppress those that act as inhibitors. The various stimuli (e.g., inflammation, diabetes and hyperphosphatemia) cause the differentiation of the VSMCs to osteoblast-like cells by promoting the production of BMPs and transcription factors (Cbfα1/Runx2, Osterix and Msx2). [See e.g., Johnson R C et al. (2006), "Vascular Calcification Pathological Mechanisms and Clinical Implications". *Circ. Res.*: 1044-1059]

VC occurs when the normal balance between inducers (BMPs, transcription factors and signal pathways) and inhibitors (MGP, OPG, OSP, PPi, fetuin) in soft tissues is disturbed by either the suppression of the inhibitors or induction of the triggers. Hence, the present invention is based on delineating the causes of VC and the mechanisms involved in calcium crystal formation and growth and identifying the combination of actives that effectively treats or prevents such abnormal calcium metabolism in soft tissues throughout the body and thereby, VC-mediated diseases. This combination of actives include (1) at least one agent that modulates expression of and/or activity of peroxisome activated protein receptor gamma (PPAR-γ); (2) at least one agent that inhibits expression and/or suppresses activity of one or more of the osteogenic transcription factors (Cbfα1/Runx2, Osterix, Msx2) and β-catenin signaling; (3) at least one agent that inhibits expression and/or suppresses activity of one or more of bone matrix proteins (BMP 2 and 4), alkaline phosphatase (ALP), and osteocalcin; (4) at least one agent that inhibits the activity of Reactive Oxygen Species (ROS); and (5) at least one agent that suppresses one or more of inflammatory mediators including interleukins IL-1α, IL-1β, IL-6, NF-κB, TNF-α, matrix metalloproteinases (MMPs) and prostaglandin E2 (PGE2). The compositions may further comprise at least one agent that promotes expression and/or carboxylation of matrix Gla protein (MGP) and/or vitamins and minerals.

It is to be understood that any one of the agents used herein may provide multiple activities or functions; thus in some embodiments the present combinations may comprise less than five or six different agents. Preferably in some embodiments, the present compositions comprise at least three phytonutrients, four or more phytonutrients in other embodiments. One embodiment of the present invention is a cardio-health product such as a dietary supplement containing phytonutrients and other bioactives that have been shown to attenuate VC by inhibiting the critical step of transforming VSMCs and other vascular cells to osteoblast-like cells. A first preferred embodiment includes a combination of bioactives such as phytonutrients and minerals and/or vitamins. Table 1 below shows examples of cardio-health formulations comprising a combination of bioactives that have been demonstrated to prevent and/or treat VC via different and sometimes overlapping mechanisms (as illustrated in Table 2). Preferred phytonutrients and other bioactives are described in more detail below.

TABLE 1

Cardio Health Dietary Supplement Compositions

| Actives (units) | Formula 1 Amt./serving | Formula 2 Amt./serving | Formula 3 Amt./serving | Formula 4 Amt./serving | Formula 5 Amt./serving |
|---|---|---|---|---|---|
| Hesperidin (mg) | 250 | | | | |
| Magnesium (mg) | 200 | 300 | 200 | 200 | 300 |
| Curcumin (mg) | 500 | 500 | 500 | 500 | 500 |
| Amorfrutin 1 (mg) | | 75 | 75 | | |
| Quercetin (mg) | 100 | 100 | 100 | 100 | 100 |
| Magnolol (mg) | | 200 | 200 | 200 | |
| Vitamin K2 (μg) | 180 | | 180 | 180 | |
| Vitamin D3 (i.u.) | | | 250 | 250 | |
| Vitamin C (mg) | 60 | | | | 60 |
| Berberine | | 300 | | | |
| Mangiferin | | 200 | | | |
| β-Boswellic Acid | | | | 500 | |
| Salicortin | | | | 200 | |
| Pycnogenol (mg) | | | 100 | | |
| Polypodium (mg) | | | | | 500 |
| Creatine (mg) | | | | | 100 |
| Resveratrol (mg) | | 100 | | | |
| Calcium (mg) | | | | 150 | |

Some of the components listed above are pure materials either isolated from natural extracts or synthesized, while some components are extracts, which may contain mixtures of active compounds. For example, Pycnogenol™ is a pine bark extract which contains procyanidin compounds; Polypodium leucotomos extract contain calagualine, a triterpenoid glycoside and several phenolic acids. In situations where it is convenient and/or cost effective, natural extracts may be substituted for pure compounds without markedly diminishing their effectiveness. For example, mangiferin may be replaced with extracts of *Mangifera indica* (mango)

and the genus *Salacia*; beta-boswellic acid by *Boswellia Serrata* extract; salicortin by *Populus balsamifera* or *Salix alba* (white willow) extract. Plant extract sources for the other pure components are described above.

TABLE 2

Cardio-Health Bioactives - Mechanisms of Action in Preventing Transformation of VSMCs to Osteogenic-Type Cells Promoters of VSMCs Differentiation

| Bioactives | BMPs | Runx2/ Cbfα1 | Osterix | β-Catenin signaling | OPG | MGP | PPAR-γ |
|---|---|---|---|---|---|---|---|
| Quercetin | | ↓ | | ↓ | | | ↑ |
| Magnesium | ↓ | ↓ | ↓ | ↓ | ↑ | ↑ | |
| Hesperidin | | | | | | | ↑ |
| Curcumin | | ↓ | | | | | |
| Magnolol | ↓ | ↓ | | | | | ↑ |
| Amorfrutins | | | | | | | ↑ |
| Vitamin K | | | | | | ↑ | |

Phytonutrients

Among phytonutrients useful in the present invention are the flavonoids and other polyphenols. Flavonoids or bioflavonoids, also known as "phenylchromones," are naturally occurring, water-soluble compounds known to have antioxidant characteristics. Flavonoids are widely distributed in vascular plants and are found in numerous vegetables, fruits and beverages such as tea and wine (particularly red wine) and therefore, are a common component of the human diet. The animal kingdom is unable to synthesize the flavone nucleus; flavonoids are therefore strictly exogenous food components of plant origin.

Flavonoids are conjugated aromatic compounds having the general structure of a 15-carbon skeleton, which consists of two phenyl rings (A and B) and a dihydropyran heterocyclic ring (C). Flavonoids are all ketone-containing compounds, such as flavones and flavonols (also referred to as anthoxanthins). This class was the first to be termed bioflavonoids. The terms flavonoid and bioflavonoid have also been more loosely used to describe non-ketone polyhydroxy polyphenol compounds, which are more specifically termed flavanoids. Flavonoids (specifically flavanoids such as the catechins, and their oligomeric forms, proanthocyanidins) are the most common group of polyphenolic compounds in the human diet and are found ubiquitously in plants. Flavonols, the original bioflavonoids such as quercetin, are also found ubiquitously, but in lesser quantities. The widespread distribution of flavonoids, their variety and their relatively low toxicity compared to other active plant compounds such as alkaloids mean that humans and animals can ingest significant quantities in their diet. Foods with high flavonoid content include parsley, onions, blueberries and other berries, apples, tea, bananas, all citrus fruits, red wine, and dark chocolate.

As of the mid 1980's more than 4000 chemically unique flavonoids have been identified and this is only a fraction of the total number likely to be present in nature. The most widely occurring flavonoids are flavones and flavonols. While the present invention is open to the use of all flavonoids, flavonols such as myricetin, (3,5,7,3',4',5',-hexahydroxyflavone), quercetin (3,5,7,3',4'-pentahydroxyflavone), kaempferol (3,5,7,4'-tetrahydroxyflavone), and flavones such as apigenin (5,7,4'-trihydroxyflavone) and luteolin (5,7,3',4'-tetrahydroxyflavone) and glycosides thereof are preferred. The main catechins are catechin [(2R, 3S)-2-(3,4-dihydroxyphenyl)-3,4-dihydro-2H-chromene-3, 5,7-triol], the cis isomer epicatechin (EC), epicatechin gallate (ECG) epigallocatechin-3-gallate (EGCG) and epigallocatechin (EGC). Although all catechins share similar properties, EGCG appears to be most potent. Some other isomers or conjugates may be present in plant sources (with either catechin or epicatechin as a backbone, and varying levels of gallic acids). Other polyphenolic compounds for use herein are structurally not flavonoids, i.e., do not contain the 15-carbon ring structure but contain the phenol functional group and may also contain the ketone group. Examples include magnolol [4-Allyl-2-(5-allyl-2-hydroxyphenyl)phenol]; curcumin [(1E,6E)-1,7-Bis(4-hydroxy-3-methoxyphenyl)-1,6-heptadiene-3,5-dione; hesperitin (5,7, 3'-trihydroxy-4'-methoxyflavanone); hesperidin (hesperitin-7-O-rutinoside); mangiferin [(1S)-1,5-anhydro-1-(1,3,6,7-tetrahydroxy-9-oxo-9H-xanthen-2-yl)-D-glucitol]; salacinol; kotalanol; resveratrol (3,5,4'-trihydroxy-trans-stilbene); p. These flavonoids and other polyphenols are preferred because each agent provides multiple biologic, health and therapeutic activities/benefits. Other phytonutrients having different chemical structures from the above flavonoids and polyphenols but having therapeutic activities are also useful herein such as certain alkaloids like berberine (5,6-dihydro-9,10-dimethoxybenzo [g]-1,3-benzodioxolo[5,6-a] quinolizinium). Because the present formulations use a combination of the above natural compounds having multiple activities, smaller amounts of each active are sufficient for therapeutic effectiveness while minimizing potential dose-dependent side effects. Some preferred flavonoids and other polyphenols are described in more detail below.

Quercetin

A preferred flavonoid for use in the invention is quercetin, which is found in many fruits and vegetables, but highest levels are found in apples, cranberries, onions, kale and broccoli. Like many other bioflavonoids, quercetin has been promoted for its anti-oxidant, anti-inflammatory, anti-atherogenic, cardioprotective, and anti-carcinogenic properties. Quercetin is ingested from the daily diet, and also widely marketed as a dietary supplement in the U.S. and Europe at doses ranging from 500 to 2000 mg per day. Beneficial effects of quercetin supplements have been reported in clinical trials. Evaluation by the International Agency for Research on Cancer (IARC) concluded that quercetin is not classified carcinogenic to humans. Quercetin has received GRAS (Generally Recognized As Safe) status, and no side-effects have yet been noted in doses of a few grams a day in either humans or animals. Quercetin may be also supplied in the present compositions as its glycosides including rutin (quercetin-3-O-rutinoside), quercitrin (quercetin 3-rhamnoside), isoquercetin (quercetin-3-glucoside aka isoquercitrin) and alpha-glycosyl isoquercetin (aka EMIQ or Enzymatically Modified Isoquercitrin). The glycosides are preferred for use herein because of their greater water solubility and absorbability and thus bioavailability as compared to quercetin itself.

It is believed that quercetin, which exhibits some of the strongest antioxidant effects of the flavonoids and which has been reported to inhibit oxidation and cytoxicity of low density lipoproteins (LDL), may have beneficial health consequences since oxidized low density lipoproteins are reported to be atherogenic, i.e., they contribute to the buildup of fatty substances in the arterial wall. Lipid peroxidation is caused by free radicals. Free radicals are molecules with at least one unpaired electron, which makes them highly reactive. Free radicals are continually formed in the metabolic processes of the human body but are tightly regulated. Human plasma contains various antioxidants which makes it difficult for such reactions to occur within the plasma. When LDL is within the arterial wall, the situation is different and the plasma antioxidant protection is not available. The reaction that can result in buildup of oxidized lipids in the arterial wall can be stopped or decreased by the presence of an antioxidant such as a flavonoid. Flavonoids appear to act by protecting LDL against oxidation, as they inhibit the generation of lipid peroxides and also may help protect alpha-tocopherol (vitamin E), a major lipophilic antioxidant carried in lipoproteins, from being consumed by oxidation in LDL. In an in-vitro study, quercetin has been shown to inhibit warfarin-mediated VC by inhibiting the differentiation of VSMCs to osteoblast-like cells [Beazley K E, et al. (2013), "Quercetin Attenuates Warfarin-induced Vascular Calcification in Vitro Independently from Matrix Gla Protein". *J. Biol. Chem.* 288: 2632-264]. Quercetin fully abolished warfarin-induced expression of osteogenic markers osteocalcin, type I collagen, and Runx2 indicating prevention of the osteoblast-like transformation of VSMCs and at the same time increased expression of osteopontin (OPN), which can act as an endogenous inhibitor of VC. Quercetin's action is mediated by inhibition of the β-catenin signaling pathway and trans-glutaminase-2. It has also been shown that quercetin intercepts the chondrogenic transformation of vascular smooth muscle and also drastically attenuates calcifying cartilaginous metaplasia in another model of VC caused by genetic loss of matrix gla protein (MGP). [Konoplyannikov M and Nurminskaya M (2014), "New therapeutic approaches to arterial calcification via inhibition of transglutaminase and β-catenin signaling". *Curr. Pharm. Des.* 2014; 20(37):5811-20.]

Furthermore, quercetin, as well as other flavonoids and polyphenols (e.g., magnolol, psi-baptigenin, apigenin, hesperidin, amorfrutins, and catechins) have been shown to function as potent agonists to peroxisome proliferator activated protein receptor gamma (PPAR-γ) [See e.g., Wang L., et al. (2014). "Natural product agonists of Peroxisome proliferator-activated receptor gamma (PPAR-γ): a review". *Biochemical Pharmacology* 92: 73-89]. PPAR-γ agonists have been used to treat diabetes, which is one of the primary triggers of VC. In an in vitro study, induction PPAR-γ has been demonstrated to inhibit the differentiation of circulating stem cells to osteoblast-like cells. [See e.g., Cho H J, et al. (2013). "Vascular Calcifying Progenitor Cells Possess Bidirectional Differentiation Potentials". *PLOS Biology* 11(e1001534): 1-15.]

Additionally, quercetin and other polyphenols such as curcumin and magnolol possess potent antibacterial and anti-inflammatory properties. For example, potent activity against oral pathogens responsible for gingivitis and periodontitis has been documented in published studies supporting their use in oral care formulations to help control gum disease. Some polyphenols are more active than others and some combinations do better than single agents. These polyphenols are active in killing bacteria as well as in controlling biofilm maturation and growth. The beneficial effects of quercetin and other polyphenols against inflammatory processes and immune responses are also well established, thereby enhancing their therapeutic potency. In vitro studies using different cells have shown that quercetin can inhibit production of inflammatory cytokines such as IL-6, IL-8 and TNF-α from human cultured mast cells and immunoglobulin E (IgE)-mediated release of histamine. [See e.g., Shahzad M et al. (2015), "Selected dietary (poly) phenols inhibit periodontal pathogen growth and biofilm formation". *Food. Funct.*, 6: 719; Palaska I, et al. (2013), "Use of Polyphenols in Periodontal Inflammation". *European J. of Pharmacology* 720: 77-83; Min Y D, et al. (2007), "Quercetin inhibits expression of inflammatory cytokines through attenuation of NF-kappaB and p38 MAPK in HMC-1 human mast cell line". *Inflamm. Res.* 56(5): 210-5; Theoharides T C, et al. (2001), "Anti-inflammatory actions of flavonoids and structural requirements for new design". *International Journal of Immunopathology and Pharmacology*, 14(3):119-127; Kimata S, et al. (2000), "Effects of luteolin, quercetin and baicalein on immunoglobulin E-mediated mediator release from human cultured mast cells". *Clinical & Experimental Allergy*, 30(4): 501-508; Askari G, et al. (2012), "The effect of quercetin supplementation on selected markers of inflammation and oxidative stress". *J. Res. Med. Sci.*, 17(7): 637-641.]

Curcumin

Curcumin is a yellow-orange pigment obtained from the plant *Curcuma longa* (turmeric) by making a powder of the dried rhizomes of the plant. It is a common ingredient in curry powders and has a long history of use in traditional Asian medicine and cooking. It is sold as an herbal supplement, cosmetics ingredient and as food flavoring and food coloring, thus being safe for human consumption. It is listed as food additive E100 in European Commission. "Food Additives". (Feb. 15, 2014). Two preliminary clinical studies in cancer patients consuming high doses of curcumin (up to 8 grams per day for 3-4 months) showed no toxicity, though some subjects reported mild nausea or diarrhea. In vitro tests suggest curcumin has quite a large safety threshold. [See e.g., Goel A; et al. (2008). "Curcumin as "Curecumin": From kitchen to clinic". *Biochemical Pharmacology* 75 (4): 787-809; Hsu C H and Cheng A L (2007), "Clinical studies with curcumin". *Advances in Experimental Medicine and Biology* 595: 471-480.]

In addition to its antibacterial activity along with quercetin as described above, curcumin has also been demonstrated to have potent antifungal activity against 23 fungi strains including *Candida* species at a fairly low concentration and to have an inhibitory effect on the adhesion of *Candida* species to human buccal epithelial cells (BEC). Since the adhesion of microorganisms to host mucosal surfaces is a prerequisite for colonization and infection, these results indicate that curcumin is a promising lead antifungal agent with none of the many side effects associated with the restricted number of commercially available antifungal drugs. [Martins C V B, et al. (2008), "Curcumin as a promising antifungal of clinical interest". *Journal of Antimicrobial Chemotherapy*, 63:2, 337-339.] The broad antimicrobial activity of curcumin along with its anti-inflammatory and antioxidant effects makes it applicable in many cosmetic, skin and hair care products. Examples include anti-dandruff shampoos, anti-aging skin creams, exfoliating cleansers, and anti-acne treatment. [See e.g., Mukherjee P K, et al. (2011), "Bioactive compounds from natural resources against skin aging". *Phytomedicine,* 19: 64-73; Shimatsu A, et al. (2012), "Clinical Application of Curcumin, A Multi-Functional Substance". *Anti-Aging Medicine,* 9(1): 43-51.]

Other areas of interest as it pertains to curcumin are alleviating cognitive decline associated with aging, being heart healthy by both electrical means and reducing lipid and plaque levels in arteries, and both reducing the risk of diabetes and being a good treatment for the side-effects associated with diabetes.

Consequently, curcumin is marketed as a supplement worldwide at concentrations ranging from 400-1000 mg. The European Food Safety Authority has concluded that curcumin when taken orally as food additive is safe for children age 1-10 years at dosages of 3 mg/kg body weight/day. Furthermore, the WHO made a recommendation that curcumin is safe for adults when taken at 150 mg/day. Also, the US FDA issued GRAS status to Curcumin C3 Complex produced by Sabinsa Corp. for use in food and beverage products.

Curcumin inherently is poorly absorbed when orally ingested by itself; thus bioavailable or absorbable forms are preferred for use in the present compositions. For example, the combination of curcumin with a small amount of piperine has been shown to increase the bioavailabity of curcumin 20-fold. [Shoba G, et al. (1998), "Influence of piperine on the pharmacokinetics of curcumin in animals and human volunteers". *Planta Med.* 64(4):353-6.] Other bioavailable forms of curcumin include a phospholipid-curcumin complex marketed as Meriva™ or Longvida™; a nanoparticulate emulsion such as Theracurmin™; a mixture of curcuminoids in their natural ratio found in turmeric prepared using a molecular dispersion process (CurcuWIN™); and a curcumin+turmeric essential oil mixture known as BCM-95 (BIOCURCUMIN™). [See e.g., Sunagawa Y, et al. (2015), "Colloidal Submicron Particle Curcumin Exhibits High Absorption Efficiency—A Double-Blind, 3-Way Crossover Study". *J. Nutr. Vitaminol.* 61:37-44]

With regard to its activity to prevent vascular calcification, the mechanism of action of curcumin is somewhat similar to that of quercetin. Both are strong antioxidants and anti-inflammatories and both reduce the expression of the osteogenic factors Cbfα1/Runx2. In an in vitro study using rat primary vascular smooth muscle cells, curcumin was demonstrated to reduce calcium plus phosphate mediated vascular calcification. The mechanism involves a reduction of transcription factors (Cbfα1/Runx2) and reactive oxygen species (ROS). The production of ROS and the expression of transcription factors are caused by oxidative stress. [See e.g., Roman-Garcia P, et al. (2011)."Natural antioxidants and vascular calcification: a possible benefit?" *J. Nephrol.* 24: 669-672; Byon C H, et al. (2008).]

Hesperidin

Hesperidin (hesperitin-7-O-rutinoside or hesperitin-7-O-rhamnosyl(1-6)glucoside) is a flavanone glycoside named after the term "Hesperidium", referring to citrus fruits which are the main source of hesperidin. Hesperidin and its aglycone (hesperitin) are common dietary flavonoids being found in many citrus products and are most well known for being concentrated in orange peels and pericarp. Hesperidin is widely known in traditional Chinese medicine alongside with naringenin as Chimpi, wherein the dried peels of citrus have been used medicinally. The actual active from hesperidin is its aglycone hesperitin (5,7,3'-trihydroxy-4'-methoxyflavanone); thus hesperidin acts like a hesperitin prodrug, i.e., supplies the body with hesperitin. After ingestion, hesperidin is hydrolyzed by gut microflora into aglycone form (hesperetin) and then conjugated mainly into glucuronides. Hesperetin and its metabolites have been reported to have several biological activities, including antioxidant, anti-inflammatory, lipid lowering, cardioprotective and neuroprotective effects; influencing bone strength and osteoblast differentiation; and ameliorating insulin resistance and endothelial dysfunction, among others. Synthetic variants of hesperidin that can be used to supply hesperitin to the body include hesperidin-7,3'-O-dimethylether (HDME), which is more lipid soluble than hesperidin and glucosyl-hesperidin (G-Hesperidin) where the aglycone (hesperitin) is not changed, but the diglycoside group has been modified into a triglycoside. This variant has increased water solubility approximately 10,000-fold relative to hesperidin but ultimately it releases hesperidin (glycone) in the body after being metabolized by intestinal α-glucosidases and then hesperidin can release free hesperitin. Another derivative that may be used to supply hesperidin in formulations is hesperidin methyl chalcone (HMC), which has been demonstrated to have high bioavailabity. Most studies using hesperidin tend to use about 500 mg of supplemental hesperidin, and use the standard form of hesperidin if taking it as a daily preventative.

Hesperidin, as a bioflavonoid, provides antioxidant benefits via enhanced activity and production of cellular antioxidant enzymes such as superoxide dismutase (SOD), heme oxygenase-1 (HO-1), catalase, etc., and elevation of the predominant cellular antioxidant called glutathione [Roohbakhsh A, et al. (2015), "Molecular mechanisms behind the biological effects of hesperidin and hesperetin for the prevention of cancer and cardiovascular diseases". *Life Sci.* 124:64-74; Kalpana K B, et al. (2009), "Evaluation of antioxidant activity of hesperidin and its protective effect on H2O2 induced oxidative damage on pBR322 DNA and RBC cellular membrane". *Mol Cell Biochem.* 323(1-2):21-9].

Often oxidative stress in the body is accompanied by systemic inflammation characteristic of many chronic conditions. Numerous studies indicate that hesperidin and hesperetin are able to reduce various pathologically elevated inflammatory markers. [See e.g., Agrawal Y O, et al. (2014), "Hesperidin produces cardioprotective activity via PPAR-γ pathway in ischemic heart disease model in diabetic rats", *PLOS One* 0111212; Tamilselvam K, et al. (2013), "Antioxidant and anti-inflammatory potential of hesperidin against 1-methyl-4-phenyl-1,2,3,6-tetrahydropyridine-induced experimental Parkinson's disease in mice", *Int. J. Nutr. Pharm. Neurol. Dis.* 3:294-302; Xiaoting L, et al. (2010), "Effect of hesperidin on expression of inducible nitric oxide synthase in cultured rabbit retinal pigment epithelial cells". *Adv. Exp. Med. Biol.* 664:193-201.] This inhibitory effect has been predominantly associated with their antioxidant activity and ability to inactivate the pro-inflammatory cascade initiated by free radicals. These compounds were also effective in decreasing the synthesis of pro-inflammatory cytokines e.g. tumor necrosis factor-alpha (TNF-α) as well as pro-inflammatory enzymes such as inducible nitric oxide synthase (iNOS), which yields nitric oxide (NO) and cyclooxygenase-2 (COX-2), which is involved in the production of inflammatory mediators such as prostaglandins.

Hesperidin is also well-known as a cardiovascular protective and strengthening agent. It demonstrates several benefits to the cardiovascular system due to its ability to affect various cellular mechanisms. For instance, due to its antioxidant properties hesperidin can prevent low density lipoprotein (LDL) oxidation and protect the cell membrane of erythrocytes (red blood cells) from oxidative damage. It also acts as an inhibitor of two main enzymes in cholesterol metabolism—HMGCoA reductase and ACAT that regulate total (so called "bad" cholesterol") and "good cholesterol" (high density lipoprotein HDL) levels. While HMG-CoA reductase is a regulatory enzyme in cholesterol biosynthesis and a primary target for statin drugs (cholesterol lowering medication), ACAT catalyzes the intracellular esterification of cholesterol and is also engaged in cholesterol absorption, hepatic secretion of very low density lipoprotein (VLDL) and cholesterol accumulation in the vascular wall [Bok S H, et al. (1999), "Plasma and hepatic cholesterol and hepatic activities of 3-hydroxy-3-methyl-glutaryl-CoA reductase and acyl CoA: cholesterol transferase are lower in rats fed citrus peel extract or a mixture of citrus bioflavonoids". *J. Nutr.* 129(6):1182-5]. Thus, by inhibiting the activity of these two enzymes hesperidin decreases the total "bad" cholesterol (LDL) and increases the "good" cholesterol (HDL). [See e.g., de Oliveira D M, et al. (2013), "Hesperidin associated with continuous and interval swimming improved biochemical and oxidative biomarkers in rats". *J. Int. Soc. Sports Nutr.* 10:27.] A study on rats fed a high cholesterol diet supplemented with flavonoids (hesperidin and naringin) demonstrated inhibition of liver cholesterol biosynthesis (28.3%) and the esterification of hepatic cholesterol (23.7%) by hesperidin. In the same study tangerine peel extract was even more potent by decreasing liver cholesterol synthesis by 37% and its esterification by 32%. These results are in agreement with others, including a human study that demonstrated a marked decrease in triglyceride level after 4 weeks of hesperidin supplementation (using G-Hesperidin, 500 mg/day). [See e.g., Kim H K, et al. (2003), "Lipid-lowering efficacy of hesperetin metabolites in high-cholesterol fed rats". *Clin. Chim. Acta,* 327(1-2): 129-37; Miwa Y, et al. (2005), "Glucosyl hesperidin lowers serum triglyceride level in hypertriglyceridemic subjects through the improvement of very low-density lipoprotein metabolic abnormality". *J. Nutr. Sci. Vitaminol.* (Tokyo) 51(6):460-70.]

Another health benefit of hesperidin has been associated with its antihypertensive effect. It is believed that hesperidin is responsible for blood pressure lowering effect of orange juice since it promotes nitric oxide production resulting in vasodilation (widening of blood vessels). Moreover, hesperidin can enhance relaxation of the endothelial cells (cells of the inner blood vessel wall) induced by the neurotransmitter acetylcholine and can inhibit secretion of endothelium-derived vasoconstricting factor endothelin-1 (ET-1) [Morand C, et al. (2011), "Hesperidin contributes to the vascular protective effects of orange juice: a randomized crossover study in healthy volunteers". *Am. J. Clin. Nutr.* 93(1):73-80]. All aforementioned mechanisms aid in blood pressure normalization.

Further, several in vitro studies have shown the inhibitory effect of hesperidin on the expression of cell adhesion molecules such as vascular cell adhesion molecule 1 (VCAM-1) and intercellular adhesion molecule 1 (ICAM-1), the proteins that participate in monocyte (type of leucocytes) recruitment and accumulation in the arterial intima (innermost layer of an artery), which are associated with the development of atherosclerosis. In addition, hesperidin exerts anti-platelet activity. Both in vitro and in vivo studies have shown the efficacy of hesperidin in suppression of platelet aggregation induced by different stimuli such as collagen, arachidonic acid, and thrombin [Jin Y R, et al. (2007), "Antiplatelet activity of hesperetin, a bioflavonoid, is mainly mediated by inhibition of PLC gamma2 phosphorylation and cyclooxygenase-1 activity". *Atherosclerosis,* 194(1): 144-52].

Magnolol

Magnolol is an active component isolated from *Magnolia officinalis* (*Magnolia* bark), typically along with its structural isomer, honokiol. Both are di-allyl biphenyl diols. The bark is stripped from the stems, branches, and roots of *Magnolia* tree, and the polyphenolic components containing magnolol and honokiol are extracted. *Magnolia officinalis* is widely used in traditional Chinese medicine to facilitate bowel movement and ameliorate abdominal fullness. In the past decades, magnolol has been characterized as an antioxidant, anti-depressant, anti-allergic, anti-cancer and antimicrobial agent. The potent antioxidant activities of magnolol and honokiol are thought to be the contribution of hydroxyl and allylic groups on a biphenolic moiety. The hydroxyl group on the biphenolic moiety results in magnolol/honokiol activity against reactive oxygen species, inhibiting cell proliferation and antimicrobial activity. Similar to quercetin, magnolol and honokiol have been demonstrated to have significant antimicrobial activity, for example, against periodontopathic microorganisms such as *Porphyromonas gingivalis, Prevotella gingivalis*, and *Actinobacillus actinomycetemcomitans* and a relatively low cytotoxic effect on human gingival cells, suggesting potential therapeutic use as a safe oral antiseptic for the prevention and the treatment of periodontal disease. [Chang B S, et al. (1998), "Antimicrobial Activity of Magnolol and Honokiol against Periodontopathic Microorganisms". *Planta Medica* 64: 367.]

A series of positive effects on the cardiovascular (CV) system have also been demonstrated for magnolol/honokiol. These effects are mostly attributed to their antioxidant activity. Excessive free radicals induce lipid peroxidation, protein denaturation and DNA damage triggering cell death. In the past 20 years, magnolol has been found to have diverse functions in different cells of the CV system. The cardiovascular protective activities of magnolol are reported to result from attenuating ischemic/reperfusion heart injury, reducing atherosclerotic change and endothelial cell apoptosis, inhibiting neutrophil activation/adhesion and vascular smooth muscle cell proliferation, preventing platelet aggregation and thrombosis, and promoting vessel relaxations. Such cardiovascular protection effects regulated by magnolol are cell-type specific and dose-related. [See e.g., Ho J H-C and Hong, C-Y (2012), "Cardiovascular protection of magnolol: cell-type specificity and dose-related effects". *Journal of Biomedical Science* 19:70.]

Safety testing of magnolol or extracts of *Magnolia* bark has been reported. In a pre-clinical study, oral administration in animals (mice: 0.625-2.5 g/kg; rat: 0.06-0.48 g/kg/day for 21 days or 0.06-0.24 g/kg/day for 90 days) of ethanol extracts (94% magnolol and 1.5% honokiol) of *Magnolia* bark neither induced drug-related side effects nor altered immune response. A randomized, double-blind, placebo-controlled clinical study for weight control among female adults showed that oral administration of capsuled extracts of *Magnolia officinalis* and *Phellodendron amurense* (250 mg, three times a day for 6 weeks) was well tolerated in both healthy and obese patients, and regulation of cortisol only in obese patients was a benefit for weight control. The oral bioavailability of magnolol is reportedly about 4-5%. To reach the therapeutic level through oral administration with 5% of oral bioavailability, 2 mg/kg per day, i.e. daily 120 mg of magnolol for a 60-kg adult, is considered sufficient for cardiovascular protection, and such a dosage is applicable and safe based on the safety studies reviewed by Ho and Hong as cited above.

With regard to vascular calcification, the benefit from magnolol results in part from its being a strong agonist of peroxisome proliferator activated receptor gamma (PPAR-γ). Magnolol functions as a PPAR-γ agonist through direct binding to the PPAR-γ ligand binding domain. A recent study demonstrated that the excellent anti-platelet and anti-thrombotic activities of magnolol are modulated by upregulation of PPAR-β/γ-dependent pathways. Magnolol (20-60 μM) dose-dependently enhanced the activity and intracellular level of PPAR-β/γ in platelets. In the presence of selective PPAR-β antagonist (GSK0660) or PPAR-γ antagonist (GW9662), the inhibition of magnolol on collagen-induced platelet aggregation and intracellular Ca mobilization was significantly reversed. [Shih C Y and Chou T C (2012), "The antiplatelet activity of magnolol is mediated by PPAR-β/γ". *Biochemical Pharmacology,* 84(6):793-803.]

As discussed above, PPAR-γ agonists such as the drugs troglitazone and rosiglitazone used to treat diabetes, have been shown to inhibit vascular calcification by suppressing the expression of osteogenic proteins including BMP-2 and the Cbfα1 transcription factor, thereby controlling differentiation of VSMCs to osteoblast-like cells and the pro-osteogenic signaling pathway and thus, VC. Magnolol is believed to have the same effect. In addition, the strong antioxidant activity of magnolol (1000 times more potent than vitamin E) prevents lipid peroxidation and the generation of reactive oxygen species (ROS), which have been shown to induce inflammation and significantly to promote osteogenic transdifferentiation of VSMCs, including upregulation and activation of Runx2/Cbfα1 in concert with matrix mineral deposition. Magnolol also promotes coronary vasodilation, reduces vessel restenosis and intimal thickening, and down regulates necrosis factor-κB (NF-κB) [See e.g., Fakhrudin N, et al. (2010), "Computer-Aided Discovery, Validation, and Mechanistic Characterization of Novel Neolignan Activators of Peroxisome Proliferator-Activated Receptors-gamma". *Mol. Pharmacol.* 77:559-566; Wang L, et al. (2014), "Natural product agonists of Peroxisome proliferator-activated receptor gamma (PPARγ): a review". *Biochemical Pharmacology* 92:73-89; Woldt, E et al. (2012) Ibid.]

Resveratrol

Resveratrol (3,5,4'-trihydroxy-trans-stilbene) is a stilbenoid, a type of natural polyphenol, produced by several plants. Sources of resveratrol in food include the skin of grapes and berries, peanuts and redwine. Like other plant polyphenols, resveratrol has potent antioxidant and anti-inflammatory activities. These activities among others have been implicated to contribute substantially to the health benefits of resveratrol. Studies have demonstrated resveratrol's capacity to favorably modulate factors involved in a number of disease models, including vascular calcification (VC), cardiovascular disease, diabetes, obesity, systemic inflammation, cancer and neurodegenerative diseases. [See e.g., Baur J A and Sinclair D A (2006). "Therapeutic potential of resveratrol: the in vivo evidence". Nat. Rev. Drug Discov. 5: 493-506; Juhasz B, et al. (2010), "Resveratrol: a multifunctional cytoprotective molecule". Curr. Pharm. Biotechnol. 11:810-818; Ning Xia, et al. (2017), "Antioxidant effects of resveratrol in the cardiovascular system". British J. Pharmacology, 174(12): 1633-1646; Vogelman B (March 2012), "How Resveratrol Combats Leading Causes of Death". LIFE EXTENSION MAGAZINE; Vang O, et al. (2011), "What is new for an old molecule? Systematic review and recommendations on the use of resveratrol". PLoS One. 6(6):e19881.]

With regard to VC and cardiovascular disease, which includes atherosclerosis, hypertension, heart attack and heart failure, resveratrol has been shown to reduce risks for these conditions by targeting multiple factors that set the stage for cardiovascular diseases. Resveratrol helps to combat high blood pressure (hypertension) by decreasing inflammatory cell infiltration into blood vessel walls and improving those vessels' ability to respond to changes in blood pressure. In addition, resveratrol has recently been shown to reduce the unfavorable remodeling and stiffening of blood vessels and heart muscle that results from sustained hypertension. [Chan V, et al. (2011), "Resveratrol improves cardiovascular function in DOCA-salt hypertensive rats". Curr. Pharm. Biotechnol. 12(3):429-36. Animal studies in pigs have shown that resveratrol helps mitigate the cholesterol elevations that result from obesity and a high-fat diet by directly regulating expression of genes that control lipid metabolism. Exposure to resveratrol triggers correction of abnormal fatty acid utilization, by inducing mitochondrial enzymes that help break down fat molecules. In pigs with the equivalent of human metabolic syndrome, resveratrol supplementation lowered body mass indices, serum cholesterol, the inflammatory marker C-reactive protein, improved glucose tolerance and endothelial function. [See e.g., Azorin-Ortuno M, et al. (2012), "Effects of long-term consumption of low doses of resveratrol on diet-induced mild hypercholesterolemia in pigs: a transcriptomic approach to disease prevention". J. Nutr. Biochem. 23(7):829-37; Bastin J, et al. (2011), "Exposure to resveratrol triggers pharmacological correction of fatty acid utilization in human fatty acid oxidation-deficient fibroblasts". Hum. Mol. Genet. 20(10):2048-57; Robich M P, et al. (2011), "Resveratrol modifies risk factors for coronary artery disease in swine with metabolic syndrome and myocardial ischemia". Eur. J. Pharmacol. 664(1-3):45-53.] As previously discussed, calcification in the arteries (VC) contributes to arterial stiffening and blockage that occurs in atherosclerosis and to the inflammatory changes that exacerbate cardiovascular disease. In addition to elevated fat and calcium content in vessel walls, aggregation of clot-forming platelets contributes to arterial blockages resulting in heart attacks, strokes, and other cardiovascular events. Studies using cultured human VSMCs, demonstrated that resveratrol diminished rosiglitazone-induced oxidative stress, osteoblast-like VSMC differentiation and mineralization, thereby reducing the amount and extent of "bone-like" calcium build-up in arterial walls. Resveratrol also limited the inflammation-inducing effects of calcium in cells lining blood vessels. Further, resveratrol inhibited the platelet aggregation that can trigger formation of a deadly blood clot. [See e.g., Takemura A, et al. (2011), "Sirtuin 1 retards hyperphosphatemia-induced calcification of vascular smooth muscle cells". Arterioscler. Thromb. Vasc. Biol. 31(9):2054-62; Gutierrez-Perez A, et al. (2011), "Protective effects of resveratrol on calcium-induced oxidative stress in rat heart mitochondria". J. Bioenerg. Biomembr. 43(2):101-7; Bruedigam C, et al. (2011), "Opposing actions of rosiglitazone and resveratrol on mineralization in human vascular smooth muscle cells". J. Mol. Cell Cardiol. 51(5):862-71; Yang Y, et al. (2011), "Inhibitory effects of resveratrol on platelet activation induced by thromboxane a(2) receptor agonist in human platelets". Am. J. Chin. Med. 39(1):145-5914.]

PPAR-γ Agonists

Also useful in the present compositions are dietary components that act as ligands of PPAR-γ including plant lipids such as n-3 and n-6 fatty acids and their derivatives, isoflavones and flavonoids discussed above. Dietary lipids include cis-5,8,11,14,17-eicosapentaenoic acid (EPA); cis-4,7,10,13,16,19-docosahexaenoic acid (DHA) and oxidized derivatives such as 4-hydroxy docosahexaenoic acid (4-HDHA) and 4-oxo docosahexaenoic acid (4-oxoDHA); linoleic acid; and eicosadienoic acid. Isoflavones include daidzein, genistein, and glycitein. Flavonoids and other polyphenols that have PPAR-γ modulating activity include quercetin, psi-baptigenin, hesperidin, hesperitin, magnolol, honokiol, EGCG, baicalein and its glucoside baicalin, Cinnamtannin B1 (in cinnamon) and rosmarinic acid (in marjoram). By PPAR-γ modulating activity is meant that the agents herein may function either as activator (up-regulator) or suppressor (down-regulator) of PPAR-γ. Human PPARs including PPAR-γ are expressed in several metabolically active tissues including liver, kidney, spleen, heart, skeletal muscle, large intestine and white and brown fat and are present in many cell types including monocytic, vascular endothelial, and vascular smooth muscle cells. Mediation of metabolic and cellular processes is very complex and depends on the particular tissue(s), cellular condition(s) and stimulated signaling pathway(s) being affected. Thus, in some instances, up-regulation of PPAR-γ activity is beneficial and suppression is beneficial in other instances. As discussed above, up-regulation of PPAR-γ expression and/or activity is beneficial for controlling the processes leading to vascular calcification.

Other Bioactives—Vitamins and Minerals

The present compositions may optionally include (a) vitamins including vitamins A, E, D, C, B2, B1, niacin B12, K (K1, K2) and folic acid and (b) minerals such as Mg, Ca, Zn, Fe, iodine. Magnesium and vitamins C, D and K are preferred components herein.

Magnesium

Magnesium is an essential mineral for the human body. It is involved in many biological reactions in the body, including glucose use, fat synthesis, muscle contraction and in the production and transport of energy and proteins. A diet rich in green, leafy vegetables, legumes, nuts, whole grains and fish is normally sufficient to meet the daily magnesium requirement. However, many people take less than the recommended dietary allowance. Low magnesium levels are often seen with malnutrition, or with the use of diuretic medicines, which can cause excessive losses of magnesium. Low Mg levels have been linked to diseases such as osteoporosis, high blood pressure, clogged arteries, heart disease, diabetes and stroke and magnesium supplements have been administered for these conditions. It has also been reported that increased consumption of magnesium is associated with reduced mortality in adults at high cardiovascular risk. [See e.g., Guasch-Ferre, M, et al (2014), "Dietary Magnesium Intake Is Inversely Associated with Mortality in Adults at High Cardiovascular Risk". *J. Nutr.* 144(1), 55-60.] The major side effect of magnesium is diarrhea, which is more common the higher the dose.

Importantly, magnesium has been shown to provide benefits against vascular calcification. Consumption of low magnesium diet has been shown to increase VC in animal models. In an in vitro study using human aortic VSMCs, magnesium was shown to prevent phosphate-mediated VC by:

(1) inhibiting the expression of BMPs, osteogenic transcription factors (Cbfα1/Runx2, Osterix) and β-catenin signaling pathway, all being involved in the transformation of VSMCS to osteoblast-type cells, (2) increasing the expression of MGP and OPG which are inhibitors of the transformation of VSMCs, and (3) interfering with hydroxyapatite crystal nucleation and growth.

Furthermore, magnesium, even at moderately elevated concentrations, was shown not only to reduce VSMC calcification, but is also able to reverse this process after it has been initiated. These findings demonstrated that magnesium has an active and significant role in the prevention and reversal of VSMC calcification. [See e.g., Montes de Oca A, et al. (2014), "Magnesium Inhibits Wnt/β-catenin Activity and Reverses the Osteogenic Transformation of Vascular Smooth Muscle Cells". *PLOS ONE* 9 (2): e89525; Nicoll R, et al. (2015), "A Review of the Effect of Diet on Cardiovascular Calcification". *Int. J. Mol. Sci.* 16: 8861-8883; Massy Z A and Drueke T B (2012), "Magnesium and outcomes in patients with chronic disease: focus on vascular calcification, atherosclerosis and survival". *Clin. Kidney,* 5 (suppl. 1): i52-i61.]

Dosing depends on the indication for which magnesium is being used. It also depends on the type of magnesium compound used, such as the chloride, sulfate, carbonate, oxide, citrate, malate, aspartate, glutamate, taurate and bisglycinate, to name a few. Preferred for use herein include the organic salts and complexes, e.g., citrate and malate and the amino acid chelated Mg complexes, such as magnesium bisglycinate, which is a soluble organic complex of Mg with the amino acid glycine. Amino acid chelated magnesium is highly bioavailable and has no gastrointestinal side effects such as diarrhea. The reported RDA for Mg is 300-400 mg/kg/day, except for people with impaired kidney function. Overall, the risk of magnesium intake at prescribed levels to healthy people is very low. The glycinate salt is readily soluble and allows for a safe level of total salt and glycine to be introduced by this complex.

Vitamin K

Vitamin K (VK) is an essential, lipid-soluble vitamin that plays a vital role in the production of coagulation proteins to help blood clotting and preventing excessive bleeding. Vitamin K is actually a group of compounds. The most important of these compounds appears to be vitamin K1 and vitamin K2. Vitamin K1 (also known as phylloquinone or phytonadione) is obtained from leafy greens and some other vegetables. Vitamin K2 is a group of compounds largely obtained from meats, cheeses, and eggs, and synthesized by the intestinal flora. In adults, Vitamin K deficiency is uncommon because of the intake of a wide variety of vegetables and other foods, the body's ability to recycle VK, and adequate gut flora production. Thus, unlike many other vitamins, VK is not typically used as a dietary supplement. An adult's daily requirement of VK has been estimated at 100-200 mcg/day, with the diet normally being a sufficient source.

Vitamin K acts as a cofactor, i.e., it is needed for the conversion of glutamic acid residues on the NH2-terminal of precursor coagulation proteins into the active form of γ-carboxyglutamic acid, which occurs via VK-dependent gamma-glutamyl carboxylase. This essential reaction allows the VK-dependent proteins to bind to surface phospholipids through calcium ion channel-mediated binding, in order to start the normal antithrombotic process. The major use of VK is treating and preventing bleeding problems in people with low levels of the blood clotting protein prothrombin and in newborns with low levels of vitamin K (hemorrhagic disease). VK is also used to reverse the effects of too much anti-coagulation caused by warfarin.

As discussed above, anti-coagulation therapy with warfarin has been demonstrated to trigger vascular calcification by inhibiting the same essential reaction, i.e., activation of matrix Gla protein (MGP) via γ-carboxylation. MGP, which is synthesized by VSMCs, functions as a calcification inhibitor. For MGP to be functional in inhibiting soft-tissue calcification, vitamin K is required as an enzymatic cofactor in the γ-carboxylation of the protein. This role of vitamin K in vascular calcification has been demonstrated in animal, human and in vitro studies as cited above. [See also Schurgers L J, et al. (2008), "Matrix Gla-protein: the calcification inhibitor in need of vitamin K". Thromb. Haemost. 100:593-603.]

Vitamin D

Vitamin D refers to a group of fat-soluble sterols that are functional in humans for increasing intestinal absorption of calcium, iron, magnesium, phosphate, and zinc. The most important compounds in this group are vitamin D3 (also known as cholecalciferol) and vitamin D2 (ergocalciferol). Cholecalciferol and ergocalciferol can be ingested from the diet and from supplements. However, very few foods contain vitamin D. Synthesis of vitamin D (specifically cholecalciferol) from 7-dehydrocholesterol in the skin of humans and most vertebrate animals by sunlight/UVB radiation exposure is the major natural source of the vitamin. Vitamin D from the diet or dermal synthesis from sunlight is biologically inactive; activation requires enzymatic conversion (hydroxylation) in the liver and kidney. In the liver, cholecalciferol (vitamin D3) is converted to calcidiol (aka 25-hydroxycholecalciferol; ergocalciferol (vitamin D2) is converted to 25-hydroxyergocalciferol (aka 25-hydroxyvitaminD2). Part of the calcidiol from vitamin D3 is converted by the kidneys to calcitriol, the biologically active form of vitamin D. Calcitriol circulates as a hormone in the blood and functions e.g., to regulate the concentration of calcium and phosphate in the bloodstream and to promote the healthy growth and remodeling of bone. Calcitriol also affects neuromuscular and immune function.

With regard to vascular calcification (VC) which involves disturbances in calcium and phosphate metabolism, the role of vitamin D and its derivatives is quite complex. It has long been reported that in humans, hypervitaminosis D (excess Vitamin D) is associated with extensive arterial calcium phosphate deposits, mostly in the form of apatite crystals. In experimental animals, the administration of pharmacological doses of vitamin D sterols has been demonstrated to lead to widespread arterial calcification, especially in association with conditions such as diabetes and chronic kidney disease (CKD). The mechanisms by which high doses of vitamin D or its derivatives induce vascular calcification include an increase in serum calcium and phosphate, a decrease in free serum levels of fetuin-A and the local induction of osteochondrogenic programs with transformation of vascular smooth muscle cells (VSMCs) into osteoblast-like cells. [See e.g., Price P A, et al. (2004), "Serum levels of the fetuin-mineral complex correlate with artery calcification in the rat". J. Biol. Chem. 279:1594-1600; Zebger Gong H, et al. (2011), "1,25-Dihydroxyvitamin D-3-induced aortic calcifications in experimental uremia: up-regulation of osteoblast markers, calcium-transporting proteins and osterix". J. Hypertens. 29:339-348; Johnson R C, et al. Ibid].

Other evidence reported in the literature suggests that a biphasic dose-response curve exists between vitamin D and vascular calcification, with adverse effects associated not only with very high vitamin D levels but also with very low levels. Negative effects associated with vitamin D excess include hyperphosphatemia, hypercalcemia, increased matrix metalloproteinase (MMP) levels, medial calcification, arterial stiffness and left ventricular hypertrophy. With vitamin D deficiency or low levels, the negative effects include increased levels of pro-inflammatory cytokines, increased MMP levels and a decrease in factors protective of endothelial cells. [See e.g., Zittermann A, et al, (2007), "Vitamin D and vascular calcification". Curr. Opin. Lipidol. 18:41-46; Drüeke T B and Massy Z A (2012), "Role of vitamin D in vascular calcification: bad guy or good guy?" Nephrol. Dial. Transplant. 27(5): 1704-1707; Haffner D, et al. (2005), "Systemic cardiovascular disease in uremic rats induced by 1,25(OH)2D3. J. Hypertens., 23:1067-1075.]

In yet other studies, beneficial effects of various active vitamin D derivatives against VC have been reported. For example, an in vitro study of high phosphate/inflammation-induced vascular calcification confirmed that the pro-inflammatory factor tumor necrosis factor-alpha (TNF-α) increased the deposition of calcium phosphate in the VSMC culture. Addition of calcitriol, the most active natural vitamin D sterol to the incubation medium drastically reduced the phosphate- and TNF-α-induced stimulation of VSMC mineralization in a concentration-dependent manner. One of the mechanisms of the vitamin D effects was downregulation of the expression of Cbfα1/Runx2 and osteocalcin, which are both involved in the osteochondrogenic process, with transformation of VSMCs to osteoblast-like cells. [See Aoshima Y, et al. (2012), "Vitamin D receptor activators inhibit vascular smooth muscle cell mineralization induced by phosphate and TNF-α". Nephrol. Dial. Transplant. 27: 1800-1806; Lopez I, et al. (2008), "The effect of calcitriol, paricalcitol, and a calcimimetic on extraosseous calcifications in uremic rats". Kidney Int. 73:300-307; Mathew S, et al. (2008), "Vitamin D receptor activators can protect against vascular calcification". J. Am. Soc. Nephrol. 19:1509-1519; Mizobuchi M, et al. (2007), "Differential effects of vitamin D receptor activators on vascular calcification in uremic rats". Kidney Int. 72: 709-715.]

Based on these findings, the appropriate dose of vitamin D or its derivatives to exert protective actions against vascular calcification would be in the physiological range, whereas high pharmacological doses might promote the vascular mineralization process. The guidelines for vitamin D intake vary in different countries. In the United States the recommended dietary allowances (RDA) of vitamin D are 600 IU/day (15 µg/day for ages 1-70 years, 800 (20 µg/day) for ages 71+ years and 400 IU/day for infants 0-12 months.

Thus the combination of the present agents provide effective inhibition of the key mechanistic processes that lead to VC, specifically, the transformation of normal/healthy vascular smooth muscle cells (VSMCs) and/or circulating stem cells to osteogenic/bone forming-like cells. Preferred combinations include quercetin, curcumin, hesperidin and magnesium. As discussed above these agents provide multiple beneficial effects including potent anti-inflammatory, anti-oxidant, and antimicrobial activities. While the initial focus of the present research was vascular calcification, it has been found that the effectiveness of the present combination of agents goes beyond VC to include benefits of calcium/mineralization management for the entire body and thus therapy and prevention of conditions such as gallstones and kidney stones and osteoporosis. Surprisingly, the present compositions have also been found to affect various mechanistic and biochemical processes that lead to undesirable conditions such as diabetes and obesity; arthritis; and impairment of bone, oral/dental and skin/hair health. Thus also contemplated herein are benefits for overall health and well-being including treatment for diabetes, obesity, arthritis, and osteoporosis and for control of plaque, calculus, gingivitis and periodontitis (oral health); skin anti-aging (via prevention of collagen and elastin degradation and control of ROS production) and hair care (for example, anti-fungal effect to control dandruff). The compositions may optionally contain additional agents having activities relevant for the specific condition being treated.

Additional Therapeutic Agents

Preferably, the present compositions do not contain additional actives other than the preferred phytonutrients, vitamins and minerals described above since the compositions as formulated with these are therapeutically effective. However, in certain embodiments, the present compositions may comprise additional therapeutic agents to obtain an optimal effect. Thus, for example, the present compositions may comprise an additional agent such as other anti-inflammatory agents, antioxidants, micronutrients and trace elements.

Other anti-inflammatory agents may include, but are not limited to, lipoxygenase inhibitors, such as nordihydroguaiaretic acid; cyclo-oxygenase inhibitors such as flurbiprofen; and non-steroidal anti-inflammatory agents such as aspirin, ketorolac, flurbiprofen, ibuprofen, naproxen, indomethacin, ketoprofen, piroxicam, meclofenamic acid, rofecoxib, celecoxib, and mixtures thereof. If present, the other anti-inflammatory agents generally comprise from about 0.001% to about 5% by weight of the compositions of the present invention.

Modifiers of cell redox status include antioxidants such as N-acetyl cysteine and gallic acid; antioxidant enzyme inducers such as anethole-dithiothione, oltipraz, pyrrolidine dithiocarbamate (PDTC) and indole-3-carbinol. Other micronutrients include Co-enzyme Q10, pyrroloquinoline quinone (PQQ), thiamine, riboflavin, niacin, pantothenic acid, pyridoxine, choline, biotin, inositol, para-aminobenzoic acid. Trace elements include manganese, chromium, molybdenum, copper, selenium and combinations thereof.

Composition Use

A safe and effective amount of the compositions of the present invention comprising the combination is typically administered to a subject in need thereof preferably from about once to four times per day, more preferably from about once to three times per day, even more preferably from about once per day to about twice per day. The period of such treatment typically can range from about one day to a lifetime. The subject may be any person or animal in need of treatment or prevention. By "animal" is meant to include in particular household pets or other domestic animals, or animals kept in captivity.

The present compositions preferably comprise magnesium in combination with three or more of phytonutrients selected from quercetin, rutin (quercetin-3-O-rutinoside), curcumin, hesperidin, hesperitin, magnolol, amorfrutins and EGCG as actives. The concentrations of the actives in the present compositions and delivered dosage of individual agents will vary depending on the type/form of composition, the intended purpose, and the gender and target age groups. Generally, each phytonutrient will be present at least about 5 mg in the composition, at least about 10 mg in some embodiments and at least about 50 mg in other embodiments. For quercetin, the preferred daily dosage is from about 10 mg to about 3,000 mg, more preferably from about 300 mg to about 2,200 mg, even more preferably from about 500 mg to about 1,500 mg. For curcumin, the preferred daily dosage is from about 10 mg to about 1,500 mg, more preferably from about 300 mg to about 1,300 mg and even more preferably about 500 mg to 1000 mg. For magnolol the preferred daily dosage is from about 5 mg to about 500 mg, more preferably about 15 mg to about 350 mg and even more preferably about 100 mg to about 300 mg. For hesperidin, the preferred daily dose is from about 5 to about 1000 mg, more preferably about 50 to about 500 mg and even more preferably about 75 to about 300 mg. For magnesium, the preferred daily dosage is from about 50 mg to about 1000 mg, more preferably from about 100 mg to about 500 mg and even more preferably from about 200 mg to about 400 mg. Vitamin K is optionally utilized in the compositions from about 10 to about 300 mcg. The compositions may be formulated for daily, weekly or monthly dosing. Preferably the compositions are formulated for daily dosing taken 1 to 4 times a day for ease of compliance in easy to swallow pills and capsules, chews, drink mixes and beverages.

The following non-limiting examples further describe preferred embodiments within the scope of the present invention. The examples are given solely for illustration and are not to be construed as limitations of this invention as many variations thereof are possible without departing from the spirit and scope thereof.

EXAMPLES

Example I. Efficacy Testing of CardioHealth Dietary Supplements

The benefits from the present compositions are demonstrated in (1) an in vitro study using human aortic VSMCs cultured under high phosphate conditions to induce calcification, (2) an in vivo feeding study using mutant mice prone to vascular calcification when fed a high phosphate diet and (3) a randomized, double-blind, placebo controlled clinical trial among adult subjects age 45-65 years. The treatment product in each study comprises as actives quercetin, curcumin, hesperidin, and magnesium. Additionally, the treatment product may include vitamin K, vitamin D and/or vitamin C.

(1) In Vitro Study

In this study conducted at Charles River laboratories, calcium content in the cells is measured following the incubation period to assess calcification. Human aortic vascular smooth muscle cells (VSMCs) were treated with elevated phosphate (Pi) to induce calcification. Degree of calcification is assessed by staining with alizarin red, which will be documented by microphotoimaging, followed by extraction and quantitation by spectrophotometry.

Test Materials:
  (1) Human aortic smooth muscle cells;
  (2) Complete Medium and Solutions DMEM (Gibco 11966-025) 20% FBS (Seradigm 1500-500) 1 mM sodium pyruvate (Gibco 11360-070) Penicillin/streptomycin (Gibco 15140-122) 20 mM HEPES (Gibco 15630-080) HBSS (Gibco 14175) Trypsin (Gibco 25200) (Lonza CC-2571);
  (3) Freezing Medium: 90% HI-FBS (Corning 35-011-CV), 10% DMSO (Sigma D2650);
  (4) Calcification Supplements: Na2HPO4 (EMD SX0720-1) NaH2PO4 (EMD SX0710-1);
  (5) Alizarin Red Staining: Alizarin Red Stain Kit (ScienCell 8678), Formaldehyde (Ricca Chemical 31908), Acetic Acid (ScienCell Kit Component #8678b), Mineral Oil (Fisher R21237), Ammonium hydroxide (ScienCell Kit Component 8678c)

(6) Ingredient Test Groups: I. Negative/Base Control, only culture media; II. Positive control, culture media+ Ca (2 mM) and Phosphate (3 mM); III. Test Group: culture media+Ca+Phosphate+Curcumin 5 µM+Quercetin 50 µM+Mg (MgCl2) 1.4 mM+Hesperidin 50 µM+Vitamin K2 10 µM Stock solutions of test and control articles were prepared in MilliQ water, filter sterilized and stored frozen. Test article and positive control concentrations were prepared fresh daily by diluting stock solutions into growth media. The test compounds were combined at the indicated concentrations and applied to VSMC in 6 well plates, with 4 replicates per combination. The test compounds were supplied as follows: Curcumin (Sigma Aldrich C7727); MgCl2 (Sigma Aldrich R0971); Hesperidin (Sigma Aldrich 1794-500MG); Vitamin K2 (Sigma Aldrich V-031-1ML); Quercetin (Tocris 1125)

VSMC Propagation and Calcification Procedures:

a. VSMCs were thawed and allowed to grow for at least a week in a 37° C., 5% CO2 incubator.

b. Cells were cryopreserved for back up use.

c. Cells were dispensed into two 6 well plates at 3,500 cells/cm2 (35,000 cells/well).

d. After the cells adhere overnight, the media was replaced with growth media alone (negative control) or supplemented to a final concentration of 3.3 mM phosphate, (by addition of 0.8 mM Na2HPO4 and 1.6 NaH2PO4 (1:2 ratio) into Gibco DMEM media, which as provided contains 1.8 mM CaCl2 and 0.9 mM NaH2PO4) with 4 wells for each treatment.

e. Cells were maintained in their respective media for 9 days, or for as long as needed, with fresh media exchanged every three to four days.

Alizarin Red Staining, Microphotography and Quantitative Extraction;

a. Media was removed and the monolayers washed with PBS. Monolayers were fixed with 10% formaldehyde for 15 min at room temperature and then washed twice with MilliQ water.

b. Monolayers were stained with Alizarin Red solution for 20 min. at room temperature with shaking.

c. Dye solution was removed and the stained monolayers washed 4 times with 4 mL/well MilliQ water while shaking for 5 min. Water is completely removed by tilting the plates for 2 min. and aspirating. Plates were stored at −20° C.

d. Staining was documented by photographing the stained monolayers under 40× magnification by phase contrast microscopy with an inverted microscope.

e. For quantitative assessment of staining, 0.8 mL 10% acetic acid was added per well, and the plates incubated with shaking for 30 min. The monolayer was removed from the plate with a cell scraper and transferred to a 1.5 mL microfuge tube. The cell suspension was overlaid with 0.5 mL mineral oil, heated to 85° C. for 10 min., then incubated on ice for 5 min.

f. The tubes were centrifuged at 20,000×g for 15 min, and 0.5 mL of the supernatant transferred to a new microfuge tube. To neutralize the acid, 0.2 mL 10% ammonium hydroxide was added per tube.

g. Aliquots of 150 µL (3 per tube) were transferred to an opaque-walled, clear bottom 96-well plate, and absorbance measured at 405 nm with a SpectraMax spectrophotometer. Data were analyzed with GraphPad Prism.

| Study Results: | | | |
|---|---|---|---|
| | Ingredient Test Groups | | |
| | 1. Base Control (Culture Media) | 2. Calcification Control (Culture Media + More Pi) | 3. Prevention (1 + 2 + SIL Technology) |
| Optical Density (OD) @ 405 nm | 0.10 | 0.65 | 0.10 |
| Change in OD relative to Control | — | +0.55 vs. 1 (Base) | 0.0 vs. base, −0.55 vs. 2 |

Result summary:
Elevated phosphate increased calcification effectively, as expected.
Optical Density, 405 nm (nanometer), Alizarin Red Stain Extraction - Higher O.D. number indicates higher calcification and lower O.D. indicates less or no calcification.
Technology under study (Quercetin + Hesperidin + Curcumin + Mg + Vitamin K2) 100% effective in preventing/shutting down calcification in human aortic VSMCs.
Units:
nm = nanometer,
µM = micromole,
mM = millimole, (2 In the feeding study, soft tissues of euthanized animals, including heart, aorta, carotid artery, kidney and liver are analyzed for calcium content using o-cresolphthalein complexone method and examined under light microscope (after Alizarin red staining) for mineralization and other lesions.

(3) In the human clinical, the biomarker osteoprotegerin (OPG) and coronary artery calcification (CAC) are measured as primary indicators of calcification status. Other changes in biomarkers or triggers of VC are also measured including inflammation (interleukins, MMPs, NF-κB, TNF-α, PGE2), hypertension (angiotensin II, blood pressure), diabetes (blood glucose, glycated hemoglobin Hb1c), Matrix Gla Protein (MGP) and bone matrix proteins: BMP2 and BMP4. Changes in bone, oral, skin/scalp, and hair health and condition are also measured using conventional markers such as dental plaque and gum redness for oral health; dandruff, itching and flaking for hair and scalp health; and elastase activity as indicator of aging mediated wrinkling of skin; OPG, bone ALP and serum procollagen type I N propeptide (PINP) as indicator of bone formation level and bone health.

The dimensions and values disclosed herein are not to be understood as being strictly limited to the exact numerical values recited. Instead, unless otherwise specified, each such dimension is intended to mean both the recited value and a functionally equivalent range surrounding that value. For example, a value or amount disclosed as "40 mg" is intended to mean "about 40 mg".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition effective against development and/or progression of vascular calcification (VC) in human and other mammalian subjects, the composition consisting essentially of:
   about 200 mg magnesium mineral supplied as a malate compound or complex;
   about 30 mg isoquercetin;
   about 100 mg resveratrol (3,5,4'-trihydroxy-trans-stilbene);
   about 90 mg curcumin; and
   optionally, about 120 mcg vitamin K2;
   wherein the composition is sufficient to reduce or inhibit transformation of vascular smooth muscle cells (VSMCs) and circulating stem cells to osteogenic cells.

2. The composition according to claim 1, formulated as a dietary or nutritional supplement in a form selected from capsules, tablets, pills, gummies, gelcaps, granules, powder, teas, drink mixes, and beverages.

3. A method of treating and controlling vascular calcification (VC) comprising administering to a subject in need thereof the composition according to claim 1, wherein the composition is sufficient to reduce or inhibit transformation of vascular smooth muscle cells (VSMCs) and circulating stem cells to osteogenic cells.

4. The method according to claim 3, wherein the composition is administered as a dietary or nutritional supplement in a form selected from capsules, tablets, pills, gummies, gelcaps, granules, powder, teas, drink mixes, and beverages.

* * * * *